United States Patent
Yamanishi et al.

(10) Patent No.: US 10,568,594 B2
(45) Date of Patent: Feb. 25, 2020

(54) CASSETTE HOLDER, AND CAPTURING PLATFORM AND MOBILE RADIATION CAPTURING APPARATUS INCLUDING CASSETTE HOLDER

(71) Applicant: Konica Minolta, Inc., Chiyoda-ku, Tokyo (JP)

(72) Inventors: Atsushi Yamanishi, Nishitokyo (JP); Hidehiko Takahashi, Hanno (JP); Takafumi Matsuo, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 295 days.

(21) Appl. No.: 15/609,601

(22) Filed: May 31, 2017

(65) Prior Publication Data
US 2018/0344270 A1 Dec. 6, 2018

(51) Int. Cl.
*A61B 6/00* (2006.01)

(52) U.S. Cl.
CPC .......... *A61B 6/4283* (2013.01); *A61B 6/4405* (2013.01)

(58) Field of Classification Search
CPC ....... A61B 6/00; A61B 6/4283; A61B 6/4405; A61B 6/44; A61B 6/0407; A61B 6/4429
USPC ................ 378/62, 167, 169, 189, 204, 208, 378/195–198
See application file for complete search history.

(56) References Cited

U.S. PATENT DOCUMENTS 3,900,405 A * 8/1975 Bartlett ................ G03G 15/758
                                                              378/167
9,006,671 B2 * 4/2015 Noguchi ............... A61B 6/4405
                                                             250/370.04
9,521,983 B2 * 12/2016 Jang ..................... A61B 6/4429

FOREIGN PATENT DOCUMENTS

| JP | H06342099 A | | 12/1994 |
|---|---|---|---|
| JP | 2000037382 A | | 2/2000 |
| JP | 2012110542 | * | 6/2012 |
| JP | 2012110542 A | | 6/2012 |

* cited by examiner

*Primary Examiner* — Jurie Yun
(74) *Attorney, Agent, or Firm* — Cantor Colburn LLP

(57) ABSTRACT

A cassette holder capable of being loaded with a radiation image capturing apparatus including a housing, a two-dimensional array of radiation detecting elements accommodated in the housing, and a connection port is shown. The cassette holder includes the following. Retention tabs hold the radiation image capturing apparatus. A connector is connectable to the connection port. The connector is magnetically fixed to the connection port. When the radiation image capturing apparatus is drawn to be detached from the cassette holder, the connector is movable with movement of the connection port. The movement of the connector moved with the connection port is regulated such that a shift distance of one end of the connector is smaller than a shift distance of the other end, and thereby the one end of the connector is detached from the connection port earlier than the other end.

13 Claims, 15 Drawing Sheets

CASSETTE HOLDER, AND CAPTURING PLATFORM AND MOBILE RADIATION CAPTURING APPARATUS INCLUDING CASSETTE HOLDER

CROSS REFERENCE TO RELATED APPLICATIONS

The present invention claims priority under 35 U.S.C. § 119 to Japanese Application No. 2015-188205 filed Sep. 25, 2015, the entire content of which is incorporated herein by reference.

BACKGROUND

1. Technological Field

The present invention relates to a cassette holder, and a capturing platform and a mobile radiation capturing apparatus that include the cassette holder. In particular, the present invention relates to a cassette holder that can be loaded with a radiation image capturing apparatus, and a capturing platform and a mobile radiation capturing apparatus that include the cassette holder.

2. Description of the Related Art

Radiographic images, such as X-ray images, captured with radiation rays are widely used for disease diagnosis, for example. Traditional radiographic images for medical use have been captured with screen films. Computed radiographic (CR) apparatuses including photostimulable phosphor sheets have been recently developed to digitalize the radiographic images. Furthermore, radiation image capturing apparatuses (flat panel detectors) have been recently developed that can detect radiation rays at a two-dimensional array of radiation detecting elements and read the radiation rays as digital image data from the radiation detecting elements.

A traditional radiation image capturing apparatus is of a dedicated type that is integrated with a support; however, a portable (also referred to as a cassette-type) radiation image capturing apparatus has been recently developed and put to practical use that includes a housing accommodating two-dimensional array of the radiation detecting elements (refer to, for example, Patent Literature 1 (Japanese Patent Application Laid-Open Publication No. H6-342099). In addition, various developments have been made to provide cassette holders that can be loaded with the portable radiation image capturing apparatuses (hereinafter simply referred to as radiation image capturing apparatuses), and capturing platforms and mobile radiation capturing apparatuses including the cassette holders (refer to, for example, Patent Literature 2 (Japanese Patent Application Laid-Open Publication No. 2000-37382)).

In some cases, a radiation image capturing apparatus loaded on a cassette holder of the capturing platform or mobile radiation capturing apparatuses transfers image data to an external device, transmits and receives signals to/from the external devices, or is supplied with electric power from the external devices, via a wired cable connected to a connector of the cassette holder (refer to, for example, Patent Literature 3 (Japanese Patent Application Laid-Open Publication No. 2012-110542).

In this case, the radiation image capturing apparatus F has a connection port Cf on a side face near a corner of the radiation image capturing apparatus F, and the connection port Cf is provided with pins p connected to the leads in a housing f of the radiation image capturing apparatus F, as illustrated in FIG. 14A, for example. With reference to FIG. 14B, the connection port Cf of the radiation image capturing apparatus F is connected to a connector Cb of the cassette holder (not shown), and the radiation image capturing apparatus F is thereby loaded on the cassette holder.

The radiation image capturing apparatus F is then connected to the external device (not shown) via the cable Ca through the connection port Cf of the radiation image capturing apparatus F and the connector Cb of the cassette holder. The radiation image capturing apparatus F transmits and receives signals to/from the external device via the cable Ca, etc. and is supplied with electric power from the external device.

In another case, the connector Cb of the cassette holder is provided with a magnet (not shown), and the connection port Cf of the radiation image capturing apparatus F is provided with a metal plate mp (shown in FIG. 14A) at a position corresponding to the position of the magnet of the connector Cb. For connection of the connector Cb to the connection port Cf, the magnet of the connector Cb of the cassette holder is fixed to the metal plate mp on the connection port Cf of the radiation image capturing apparatus F. Such a configuration can ensure the connection between the connection port Cf of the radiation image capturing apparatus F and the connector Cb of the cassette holder.

Unfortunately, the configuration in which the connection port Cf of the radiation image capturing apparatus F is magnetically fixed to the connector Cb of the cassette holder hinders detachment of the connection port Cf of the radiation image capturing apparatus F from the connector Cb of the cassette holder when the radiation image capturing apparatus F is detached from the cassette holder, compared with a configuration in which the connection port Cf is not magnetically fixed to the connector Cb.

In detail, in order to detach the radiation image capturing apparatus F from the cassette holder, relatively large force should be applied to the radiation image capturing apparatus F and the connector Cb in opposite directions perpendicular to the contacting face between the radiation image capturing apparatus F and the connector Cb, as indicated by the arrows in FIG. 14B.

As described above, the configuration in which the connection port Cf of the radiation image capturing apparatus F is magnetically fixed to the connector Cb of the cassette holder ensures the connection between the connection port Cf and the connector Cb, but hinders the detachment of the radiation image capturing apparatus F from the cassette holder.

SUMMARY

An object of the present invention, which has been made in view of these problems described above, is to provide a cassette holder having a connector that can be appropriately and readily detached from the connection port of the radiation image capturing apparatus when the radiation image capturing apparatus is detached from the cassette holder, and a capturing platform and a mobile radiation capturing apparatus that include the cassette holder.

To achieve at least one of the abovementioned objects, according to an aspect of the present invention, a cassette holder reflecting one aspect of the present invention is a cassette holder capable of being loaded with a radiation image capturing apparatus including a housing, a two-dimensional array of radiation detecting elements accommodated in the housing, and a connection port, the cassette holder including: retention tabs to hold the radiation image capturing apparatus loaded on the cassette holder; and a connector connectable to the connection port of the radiation image capturing apparatus held by the retention tabs, wherein when the connector is connected to the connection port, the connector is magnetically fixed to the connection port, when the radiation image capturing apparatus is drawn to be detached from the cassette holder, the connector is movable with movement of the connection port magnetically fixed to the connector, and the movement of the connector moved with the connection port is regulated such that a shift distance of one end of the connector is smaller than a shift distance of the other end of the connector, and thereby the one end of the connector is detached from the connection port of the radiation image capturing apparatus earlier than the other end of the connector.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DESCRIPTION OF THE PREFERRED EMBODIMENTS

Hereinafter, one or more embodiments of the present invention will be described with reference to the drawings. However, the scope of the invention is not limited to the disclosed embodiments.

The cassette holder of the present invention can be loaded on the capturing platform or the mobile radiation capturing apparatus and also can be used independently.

The following description will be focused on a capturing platform designed for supine radiography. The present invention, however, is also applicable to a capturing platform designed for standing radiography.

<Basic Configuration of Capturing Platform>

Figure 1:
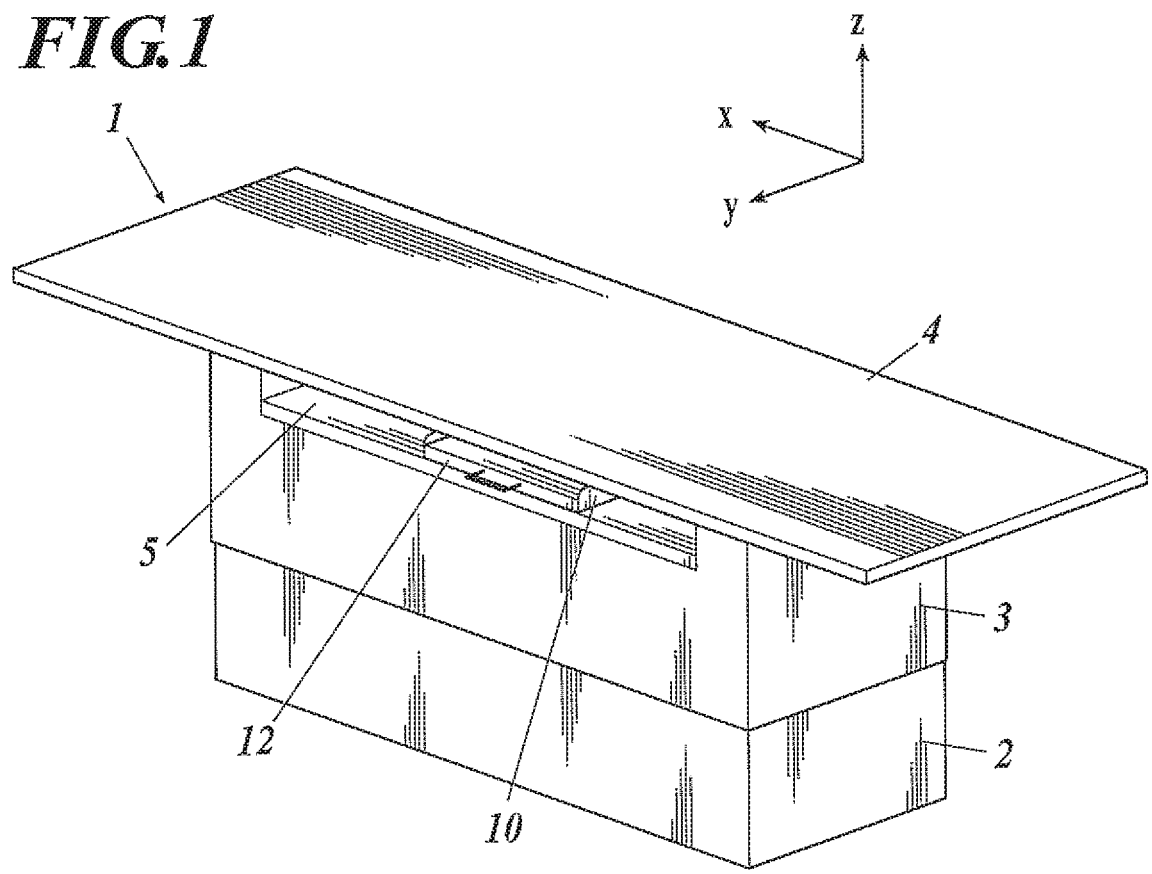
FIG. 1 is a perspective view of the external appearance of a capturing platform according to an embodiment of the present invention.

FIG. 1 is a perspective view of a capturing platform 1 according to an embodiment of the present invention. In this embodiment, the capturing platform 1 has a base 2 fixed on the floor (not shown), a support 3 held by the base 2 from underneath, and a top panel 4 supported by the support 3 from underneath. A patient (not shown) lies on the top panel 4. The support 3 and the top panel 4 can be moved relative to the base 2 in the vertical direction (i.e., along z-axis in the drawing) by a lifting mechanism (not shown). The top panel 4 can also be moved in a horizontal direction (i.e., along x-axis and y-axis in the drawing) by a moving mechanism (not shown).

A storage space 5 is provided above the support 3 and immediately below the top panel 4. The storage space 5 accommodates a cassette holder 10 that can be loaded with a radiation image capturing apparatus F (not shown). The position of the cassette holder 10 can be shifted along x-axis in FIG. 1 (i.e., the extending direction of the top panel 4) in the storage space 5. The position of the cassette holder 10 may also be changed along y-axis in FIG. 1 in the storage space 5.

<Configuration of Cassette Holder>

The configuration of the cassette holder 10 of the capturing platform 1 according to an embodiment of the present invention will now be described. In some descriptions on the components of the cassette holder 10, the cassette holder 10 is disposed such that the "frontward" side of the cassette holder 10 is directed to the near side of y-axis and the "rearward" side of the cassette holder 10 is directed to the far side of y-axis, as illustrated in FIG. 1.

Figure 2:
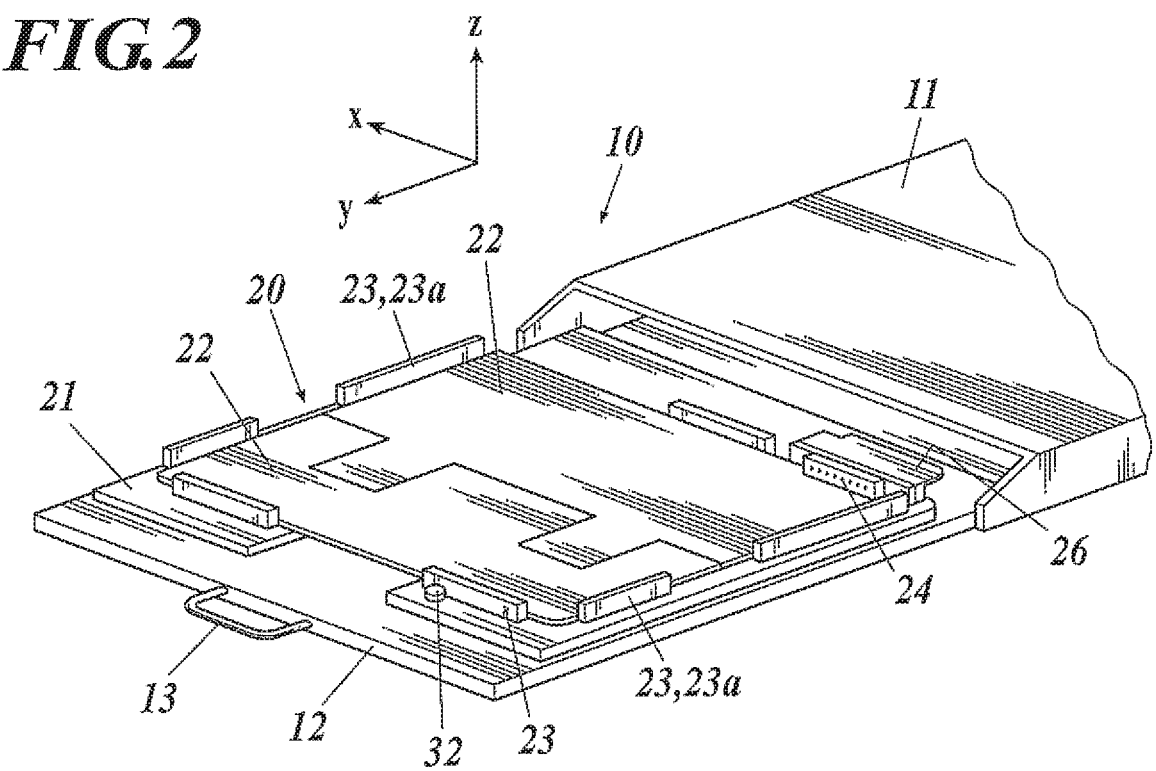
FIG. 2 illustrates a tray drawn from a cassette holder according to an embodiment of the present invention.

With reference to FIG. 2, the cassette holder 10 of the capturing platform 1 according to the embodiment has a cover 11 accommodating a tray 12. The tray 12 is drawable frontward and retractable rearward from/into the cover 11 along tracks (not shown). The tray 12 is provided with a handle 13 with which a radiological technologist draws or retracts the tray 12.

FIG. 2 illustrates the tray 12 drawn from the cover 11 of the cassette holder 10, and FIG. 1 illustrates the tray 12 retracted in the cassette holder 10. It should be noted that components other than the cassette holder 10 of the capturing platform 1 are not depicted in FIG. 2 and the subsequent drawings.

A retention section 20 is provided on the upper side of the tray 12. The retention section 20 includes retention tabs 23 to hold the radiation image capturing apparatus F. The retention section 20 is mainly composed of a turn table 21, slide tables 22, the retention tabs 23, and a connector 24. The connector 24 is provided with a cable 25 (refer to FIGS. 4A and 4B), which is not illustrated or part of which is illustrated in FIG. 2 and the subsequent drawings. The cable 25 actually extends to the rear face (bottom side in this embodiment) of the tray 12 and into the cassette holder 10.

The turn table 21 having a substantially flat shape is attached on the upper side of the tray 12. In this embodiment, the turn table 21 is turnable on the tray 12 as described below. A turn of the turn table 21 relative to the tray 12 turns the entire retention section 20, which is described later.

The two slide tables 22 are attached on the upper side of the turn table 21. The slide tables 22 are movable parallel to the turn table 21 and openable in opposite directions, which will be described later. The following description is based on the assumption that the turn table 21 does not turn and the slide tables 22 are being closed, unless otherwise specified. A stopper 32 illustrated in FIG. 2 will be described later.

Each retention tab 23 is an upward extension of the slide table 22. Alternatively, the retention tabs 23 may be separate components attached to the ends of the slide tables 22. After the radiation image capturing apparatus F (not shown) of 14-by-17-inches is loaded on the upper faces of the slide tables 22, the retention tabs 23 abut on the respective sides of the loaded radiation image capturing apparatus F so as to hold the radiation image capturing apparatus F and to prevent the movement of the radiation image capturing apparatus F in horizontal directions (i.e., along x- and y-axes).

As described above, the turn table 21 and the slide tables 22 of the cassette holder 10 according to the embodiment function as a support base to hold the rear face of the loaded radiation image capturing apparatus F.

The connector 24 is positioned behind the rearward side of the slide table 22. The connector 24 is connected to the connection port Cf (refer to FIG. 3A) provided on a side face of the housing f when the radiation image capturing apparatus F is loaded on the upper faces of the slide tables 22.

Figure 3A:
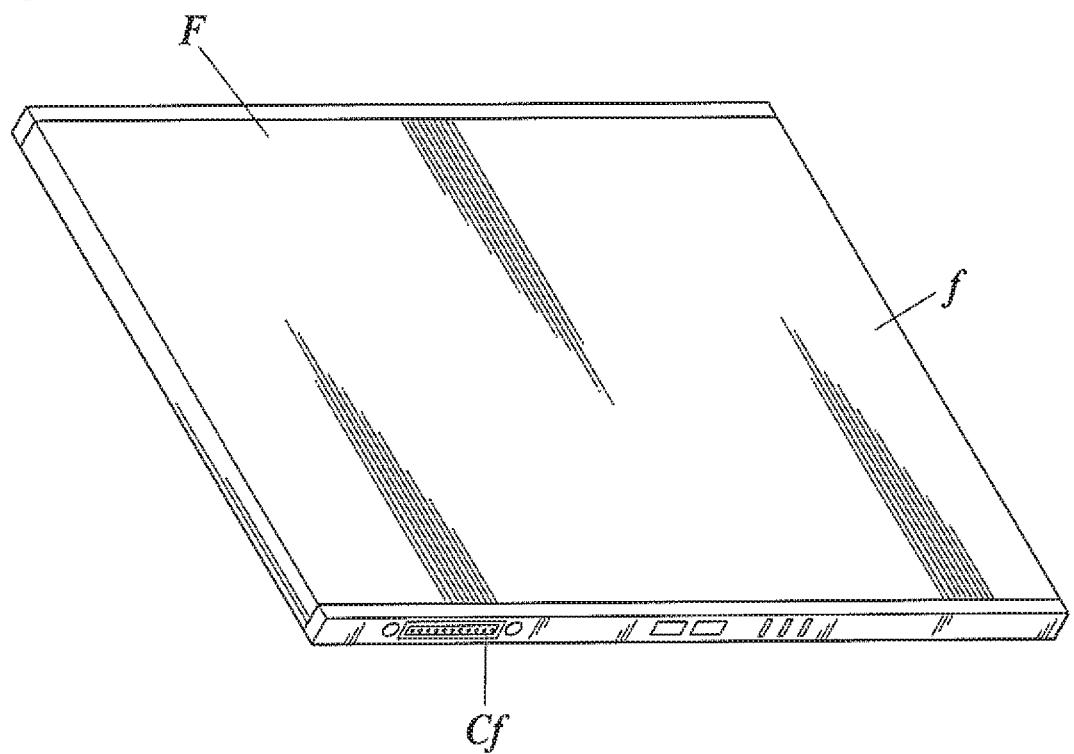
FIG. 3A illustrates the position of a connection port of a radiation image capturing apparatus.
Figure 3B:
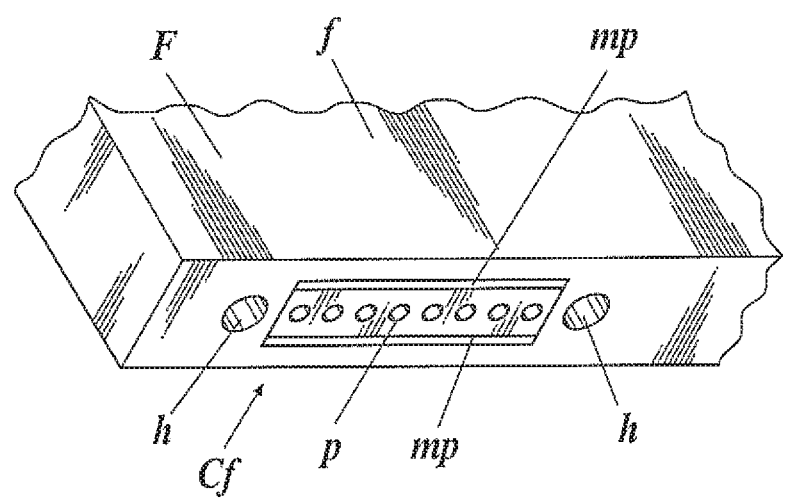
FIG. 3B is an enlarged view of the connection port of the radiation image capturing apparatus.
Figure 14A:
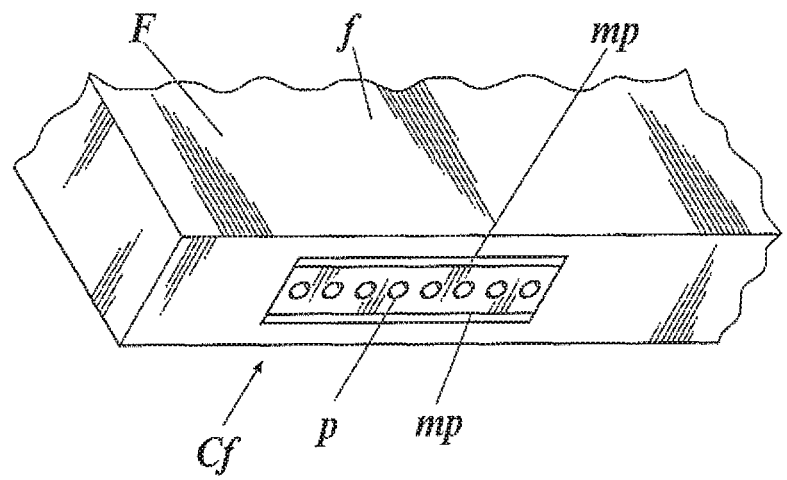
FIG. 14A illustrates an example connection port of a typical radiation image capturing apparatus.

As illustrated in FIGS. 3A and 3B, the connection port Cf of the radiation image capturing apparatus F according to the embodiment is disposed on a side face near a corner of the radiation image capturing apparatus F. Like the connection port Cf illustrated in FIG. 14A described above, the connection port Cf according to the embodiment is provided with flat pins p connected to the leads extending in the housing f of the radiation image capturing apparatus F and a metal plate mp configured to be magnetically fixed to a magnet 24c (refer to FIGS. 4A and 4B described below) provided on the connector 24 of the cassette holder 10.

The connection port Cf of the radiation image capturing apparatus F according to the embodiment has holes h into which positioning pins 24d (refer to FIGS. 4A and 4B described below) of the connector 24 are inserted when the connector 24 of the cassette holder 10 is connected to the connection port Cf. Such a configuration according to the embodiment allows the positioning pins 24d to be inserted in the respective holes h when the connection port Cf of the radiation image capturing apparatus F is automatically connected (described below) to the connector 24 of the cassette holder 10, facilitating appropriate automatic positioning of the connection port Cf and the connector 24.

<Configuration of Connector>

The connector 24 of the cassette holder 10 will now be described. In this embodiment, the connector 24 has a predetermined number of pins 24b protruding from a support 24a. Magnets 24c fixed to the support 24a are disposed adjacent to the two sides of each pin 24b, as described in FIGS. 4A and 4B.

The tip of each pin 24b of the connector 24 protrudes beyond the magnets 24c. The pins 24b are movable in the axial direction of the pins 24b relative to the support 24a, and are biased by urging members, such as springs, (not shown) in a protruding direction (i.e., the front direction in FIG. 4A or the downward direction in FIG. 4B).

Positioning pins 24d protrude from the face of the support 24a of the connector 24 provided with the pins 24b. As described above, the positioning pins 24d are inserted in the respective holes h (refer to FIG. 3B) provided in the connection port Cf of the radiation image capturing apparatus F when the connector 24 is connected to the connection port Cf of the radiation image capturing apparatus F. Such a configuration facilitates automatic positioning of the connection port Cf of the radiation image capturing apparatus F relative to the connector 24.

Figure 4A:
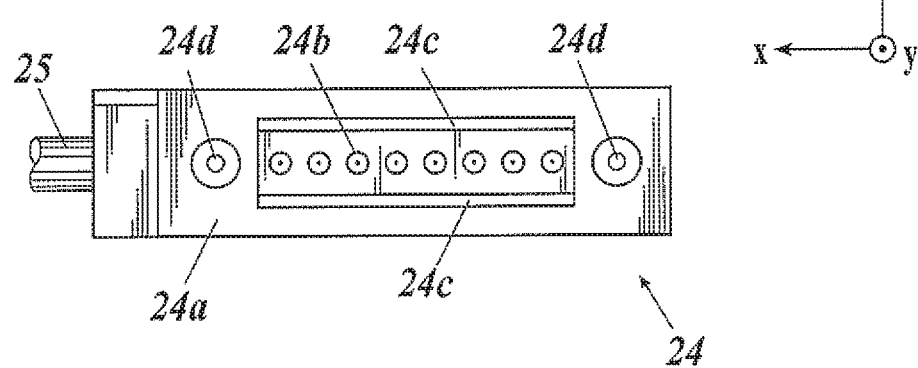
FIG. 4A is a front view of a connector of the cassette holder of the capturing platform.
Figure 4B:
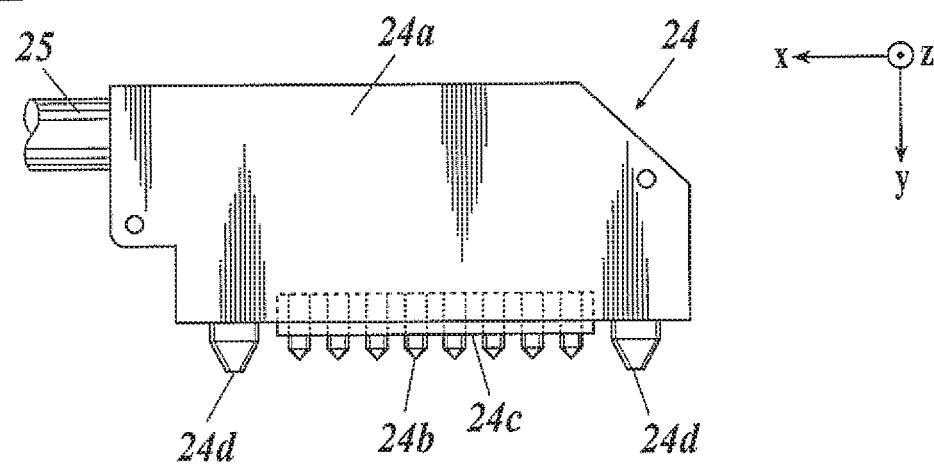
FIG. 4B is a plan view of the connector illustrated in FIG. 4A.

In this embodiment, as illustrated in FIGS. 4A and 4B, the positioning pins 24d of the connector 24 each have a tapered tip so as to be securely inserted in the corresponding hole h in the connection port Cf of the radiation image capturing apparatus F. In addition, as illustrated in FIGS. 4A and 4B, a cable 25 including leads (not shown) connecting to the respective pins 24b of the connector 24 is connected to the support 24a of the connector 24.

Since the connector 24 and the other components according to the embodiment have the configurations described above, the tips of the positioning pins 24d of the connector 24 are inserted in the respective holes h in the connection port Cf of the radiation image capturing apparatus F and the tips of the pins 24b of the connector 24 abut on the flat pins p on the connection port Cf of the radiation image capturing apparatus F, when the connection port Cf of the radiation image capturing apparatus F is connected to the connector 24 of the cassette holder 10.

For closer connection between the connection port Cf of the radiation image capturing apparatus F and the connector 24, the positioning pins 24d of the connector 24 are inserted in the respective holes h in the connection port Cf of the radiation image capturing apparatus F, the pins 24b of the connector 24 come into pressure contact with the pins p of the connection port Cf of the radiation image capturing apparatus F, and the magnets 24c of the connector 24 are magnetically fixed to the metal plate mp of the connection port Cf of the radiation image capturing apparatus F by the magnetic force of the magnets 24c of the connector 24.

In this way, the positioning pins 24d facilitate appropriate automatic positioning of the connection port Cf of the radiation image capturing apparatus F relative to the connector 24 of the cassette holder 10 for the connection therebetween, and secure the connection between the pins 24b of the connector 24 and the pins p of the connection port Cf of the radiation image capturing apparatus F.

Alternatively, the connection port Cf of the radiation image capturing apparatus F may be provided with magnets, and the connector 24 may be provided with a metal plate. The connection between the connection port Cf of the radiation image capturing apparatus F and the connector 24 of the cassette holder 10 will be described in detail below.

<Configuration of Retainer of Connector>

Figure 5A:
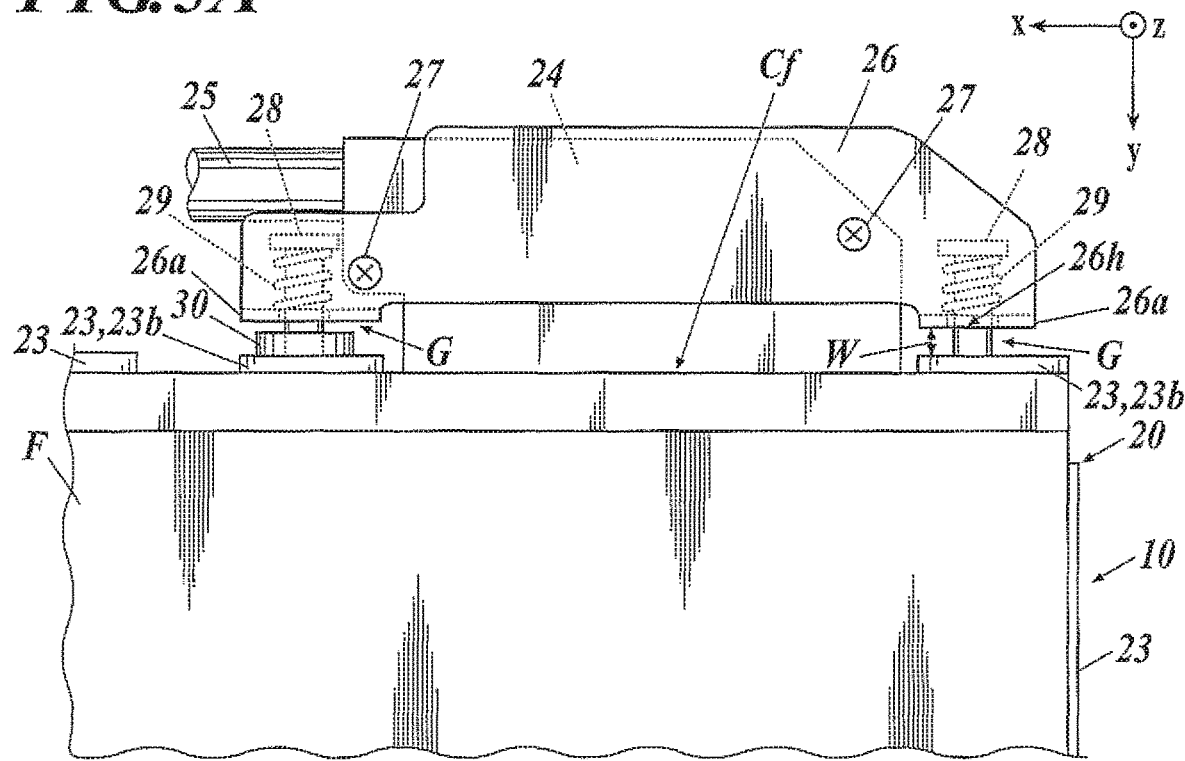
FIG. 5A is a plan view illustrating connection between the connector of the cassette holder and the connection port of the radiation image capturing apparatus loaded on a retention section of the cassette holder.
Figure 5B:
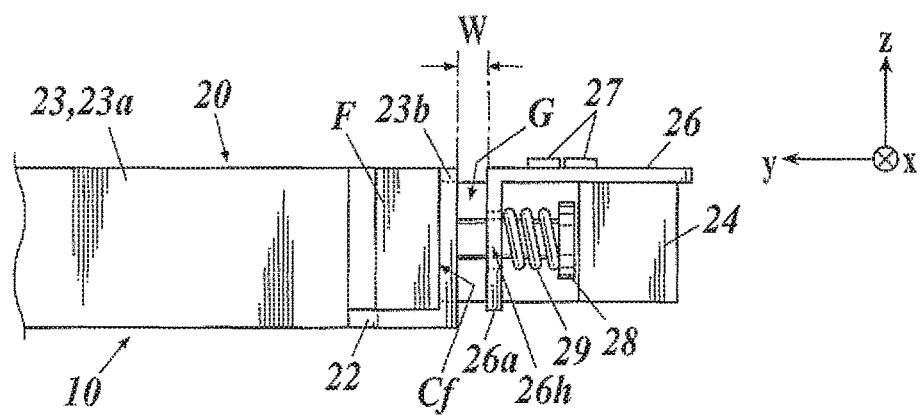
FIG. 5B is a side view of the connection illustrated in FIG. 5A.

A retainer 26 of the connector 24 according to the embodiment will now be described. FIG. 5A is a plan view of the connecting portion of the connector 24 and the connection port Cf of the radiation image capturing apparatus F loaded on the retention section 20 of the cassette holder 10, and FIG. 5B is a cross-sectional view thereof.

In this embodiment, the retainer 26 of the connector 24 has a plate shape and is fixed on the upper surface of the connector 24 with screws 27. The retainer 26 has two bent portions 26a extending downward and residing adjacent to the retention section 20 of the cassette holder 10. Part of the connector 24 provided with the pins 24b (refer to FIGS. 4A and 4B) protrudes through a gap between the two bent portions 26a toward the retention section 20 of the cassette holder 10 (i.e. in the front direction). It is noted that the pins 24b of the connector 24 are not depicted in FIG. 5 and the subsequent drawings (except FIG. 9 described below).

The retention section 20 of the cassette holder 10 is provided with the retention tabs 23, as described above. With reference to FIGS. 5A and 5B, two of the retention tabs 23 respectively face the two bent portions 26a of the retainer 26 after the connector 24 is connected to the connection ports Cf of the radiation image capturing apparatus F loaded on the retention section 20 and supported by the retention tabs 23. The two retention tabs 23 are hereinafter referred to as retention tabs 23b.

In this embodiment, two guide rods 28 respectively protrude rearward from the retention tabs 23b (upward in FIG. 5A or rightward in FIG. 5B) in a horizontal direction. Each of the guide rods 28 is inserted in a corresponding hole 26h in the bent portion 26a of the retainer 26 of the connector 24 and thus extends rearward through the bent portion 26a.

A spring 29 is disposed around part of each guide rod 28 residing behind the bent portion 26a. The front end (lower end in FIG. 5A or left end in FIG. 5B) of the spring 29 is fixed to the bent portion 26a, and the rear end of the spring 29 is fixed to a spring retainer at an end of the guide rod 28. The connector 24 and the retainer 26 are thereby urged by the springs 29 toward the retention section 20 of the cassette holder 10 (i.e., toward the front).

With reference to FIGS. 5A and 5B, the connector 24 connected to the connection port Cf of the radiation image capturing apparatus F loaded on the retention section 20 of the cassette holder 10 is biased in the rearward direction opposite to the urging direction of the springs 29 (i.e., apart from the retention section 20 of the cassette holder 10), and the springs 29 are thereby compressed from the natural lengths.

In this embodiment, the connector 24 protrudes through the gap between the two bent portions 26a of the retainer 26 toward the retention section 20 of the cassette holder 10, as described above. With reference to FIGS. 5A and 5B, while the connector 24 is connected to the connection port Cf of the radiation image capturing apparatus F loaded on the retention section 20, a gap G is defined between each bent portion 26a of the retainer 26 and the corresponding retention tab 23b of the retention section 20.

When a radiological technologist draws the radiation image capturing apparatus F frontward (i.e., downward in FIG. 5A or leftward in FIG. 5B) to detach the radiation image capturing apparatus F from the cassette holder 10, the gaps G between the bent portions 26a of the retainer 26 and the retention tabs 23b of the retention section 20 allow the connector 24 magnetically fixed to the connection port Cf of the radiation image capturing apparatus F and the retainer 26 to move frontward with the movement of the connection port Cf connected to the connector 24 and the retainer 26.

In this embodiment, a regulator 30 is disposed between one of the bent portions 26a (on the left in FIG. 5A) of the retainer 26 and the corresponding retention tab 23b. The regulator 30 reduces the width W of the gap G between the one bent portion 26a (on the left in FIG. 5A) of the retainer 26 and the corresponding retention tab 23b, compared to the width W of the other gap G between the other bent portion 26a (in the right in FIG. 5A) of the retainer 26 and the corresponding retention tab 23b.

In this embodiment, the regulator 30 is a metal washer fit around the guide rod 28, as illustrated in FIG. 5A. Besides a washer, the regulator 30 may be any component that can adjust the width W (shift distance, described below) of the gap G. For example, the regulator 30 may be part of a guide rod 28 having a diameter larger than the remaining part of the guide rod 28.

<Operation>

The operation of the capturing platform 1 and the cassette holder 10 according to the embodiment of the present invention will now be described. In this embodiment, the regulator 30 adjusts the width W of the gap G between one of the bent portions 26a (on the left in FIG. 5A) of the retainer 26 and the corresponding retention tab 23b to be less than the width W of the other gap G between the other bent portion 26a (in the right in FIG. 5A) of the retainer 26 and the corresponding retention tab 23b, as described above.

To detach the radiation image capturing apparatus F from the cassette holder 10, the radiological technologist draws the tray 12 frontward from the position illustrated in FIG. 1 to the position illustrated in FIG. 2, as described above (the radiation image capturing apparatus F is not depicted in FIG. 2). The radiological technologist then lifts up a front portion (front portion in FIG. 2, lower portion in FIG. 5A, and left portion in FIG. 5B) of the radiation image capturing apparatus F held by the retention section 20 of the cassette holder 10, and draws the lifted radiation image capturing apparatus F frontward.

After the radiation image capturing apparatus F is drawn frontward, the connector 24 connected to the connection port Cf of the radiation image capturing apparatus F and the retainer 26 are moved frontward with the movement of the radiation image capturing apparatus F. As described above, the regulator 30 is disposed adjacent to one of the bent portions 26a of the retainer 26, so that the width W of the gap G adjacent to the one bent portion 26a is smaller than that adjacent to the other bent portion 26a, in this embodiment.

Figure 6A:
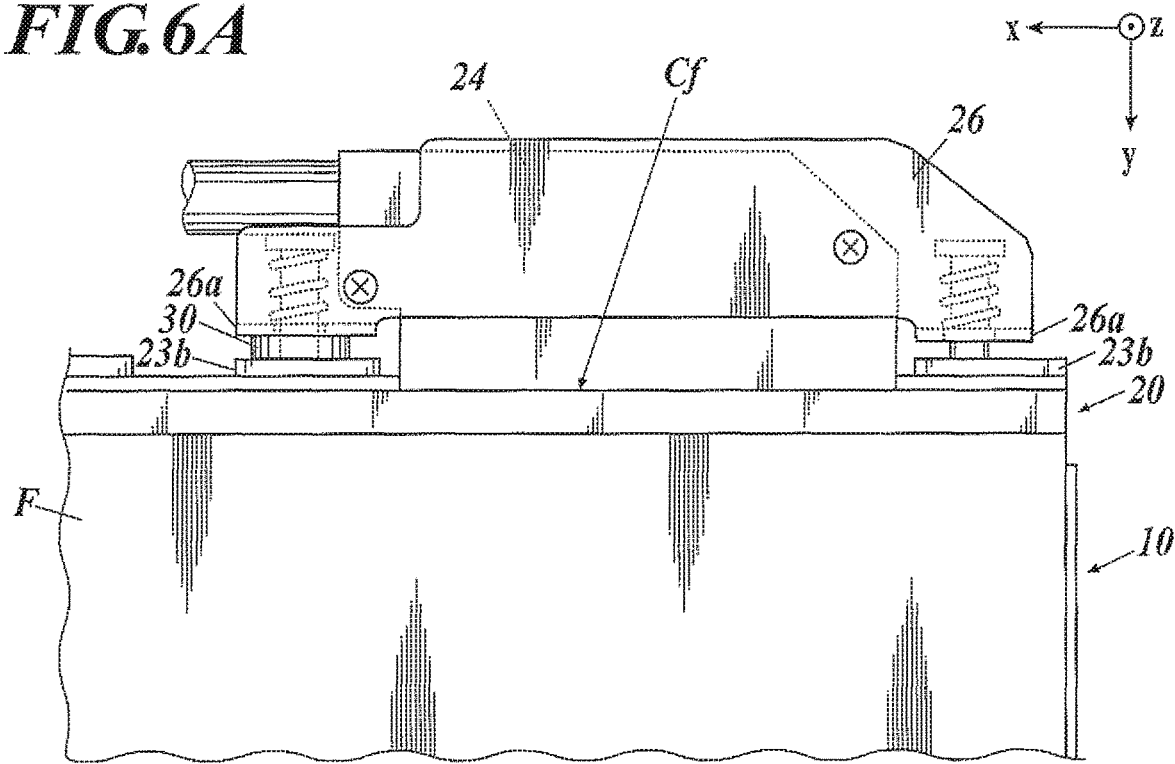
FIG. 6A illustrates the state where a bent portion disposed at one end of a retainer is in contact with a regulator, when the radiation image capturing apparatus is detached.

Such a configuration allows the one bent portion 26a (on the left in FIG. 6A) of the retainer 26 to come into contact with the regulator 30, as illustrated in FIG. 6A, after the movement of the connector 24 and the retainer 26 with the movement of the radiation image capturing apparatus F and the connection port Cf. The regulator 30 prevents the one bent portion 26a of the retainer 26 from moving forward and thus hinders frontward movement of one end of the connector 24.

In contrast, the other bent portion 26a (in the right in FIG. 6A) of the retainer 26 can move forward because the regulator 30 is not disposed adjacent to the other bent portion 26a. When the radiological technologist draws the radiation image capturing apparatus F further frontward, the one end of the connector 24 does not move forward, whereas the other end of the connector 24 moves frontward with the movement of the radiation image capturing apparatus F. The one end of the connector 24 is thereby detached from the connection port Cf of the radiation image capturing apparatus F earlier than the other end of the connector 24, as illustrated in FIG. 6B.

In this embodiment, the regulator 30 is disposed only adjacent to one of the two bent portions 26a of the retainer 26 fixed to the connector 24; hence, the shift distance of the one ending portion of the retainer 26 (i.e., the width W of the gap G between the one bent portion 26a and the corresponding retention tab 23b) is less than that of the other ending portion of the retainer 26 (i.e., the width W of the gap G between the other bent portion 26a and the corresponding retention tab 23b), as described above.

When the radiological technologist draws to detach the radiation image capturing apparatus F from the cassette holder 10, the connector 24 and the retainer 26 are moved frontward with the movement of the connection port Cf of the radiation image capturing apparatus F, one end of the retainer 26 is brought into contact with the regulator 30 and prevented from moving forward by the regulator 30, and then the other end of the retainer 26 moves further forward. The radiological technologist draws the radiation image capturing apparatus F further forward, so that the one end of the connector 24 is detached from the connection port Cf of the radiation image capturing apparatus F earlier than the other end of the connector 24, as illustrated in FIG. 6B.

Figure 6B:
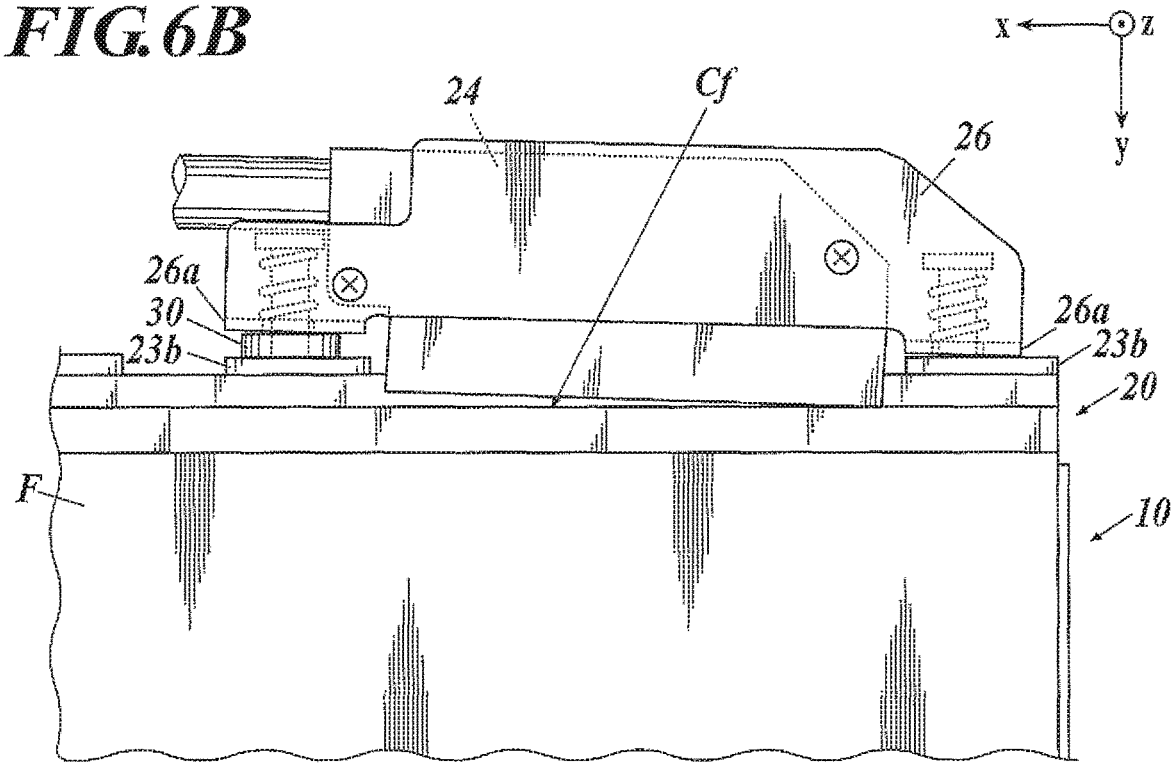
FIG. 6B illustrates the state where one end of the connector is detached from the connection port of the radiation image capturing apparatus earlier than the other end of the connector.

The radiological technologist draws the radiation image capturing apparatus F further forward from the position illustrated in FIG. 6B, so that the frontward movement of the other end of the connector 24 is hindered by the retention tab 23b. The other end of the connector 24 is thereby detached from the connection port Cf of the radiation image capturing apparatus F. The connection port Cf of the radiation image capturing apparatus F is thus disconnected from the connector 24 of the cassette holder 10.

In this embodiment, the radiological technologist can appropriately disconnect the connection port Cf of the radiation image capturing apparatus F from the connector 24 of the cassette holder 10 with such a simple operation of drawing the radiation image capturing apparatus F frontward.

Furthermore, in this embodiment, when the connection port Cf of the radiation image capturing apparatus F is disconnected from the connector 24 of the cassette holder 10, the regulator 30 allows one end of the connector 24 to be automatically detached from the connection port Cf of the radiation image capturing apparatus F earlier than the other end of the connector 24 (refer to FIG. 6B), as described above.

Figure 14B:
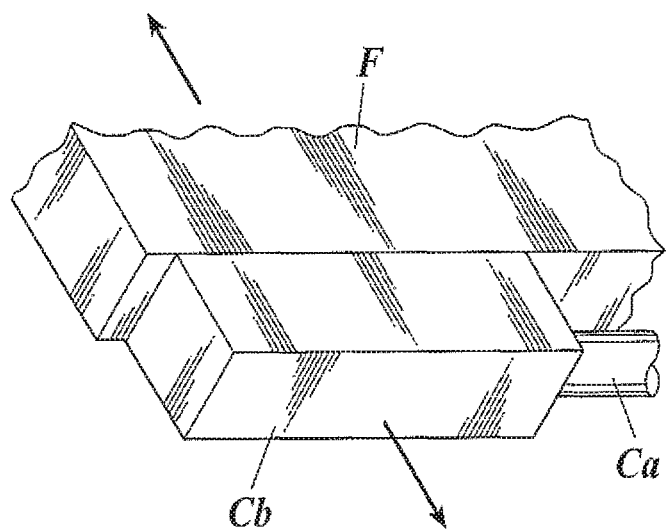
FIG. 14B illustrates removal of the connection port of the radiation image capturing apparatus magnetically fixed to the connector by the force in opposite directions perpendicular to the contacting face between the connection port and the connector.

Unlike the connector Cb illustrated in FIG. 14B, which is disconnected at once from the connection port Cf of the radiation image capturing apparatus F magnetically fixed to the connector Cb, the connector 24 of this embodiment, illustrated in FIG. 6B, is detached from the connection port Cf of the radiation image capturing apparatus F at one end first, and then at the other end. Accordingly, the connection port Cf of the radiation image capturing apparatus F can be disconnected from the connector 24 of the capturing platform 1 of the radiation image capturing apparatus F in a very simple manner, in comparison with the disconnection of the connection port Cf of the radiation image capturing apparatus F from the connector Cb of the capturing platform illustrated in FIG. 14B.

Advantageous Effect

As described above, when the radiation image capturing apparatus F is drawn to be detached from the cassette holder 10 of the capturing platform 1 according to the embodiment, the regulator 30 hinders the movement of the connector 24 such that the shift distance W of one end of the connector 24 (i.e., the width W of the gap G; the same is applied to the description below) with the movement of the connection port Cf of the radiation image capturing apparatus F magnetically fixed to the connector 24 is smaller than the shift distance W of the other end of the connector 24. Such a configuration allows the one end of the connector 24 to be detached from the connection port Cf of the radiation image capturing apparatus F earlier than the other end of the connector 24.

Accordingly, the radiological technologist can appropriately and readily disconnect the connection port Cf of the radiation image capturing apparatus F from the connector 24 of the capturing platform 1 when the radiation image capturing apparatus F is detached from the capturing platform 1.

<Modification 1 of Connector and Retainer>

In the above embodiment, the cassette holder 10 and the capturing platform 1 having the following configuration are described: As illustrated in FIG. 5A, the retainer 26 is disposed such that the bent portions 26a at the two ends of the retainer 26 are parallel to the respective retention tabs 23b, while the radiation image capturing apparatus F is loaded on the retention section 20 of the cassette holder 10. The regulator 30 disposed adjacent to one of the bent portions 26a of the retainer 26 reduces the width W (or shift distance W) of the gap G defined between the one bent portion 26a of the retainer 26 and the corresponding retention tab 23b, compared to the width W (or shift distance W) of the gap G defined between the other bent portion 26a of the retainer 26 and the corresponding retention tab 23b.

Figure 7:
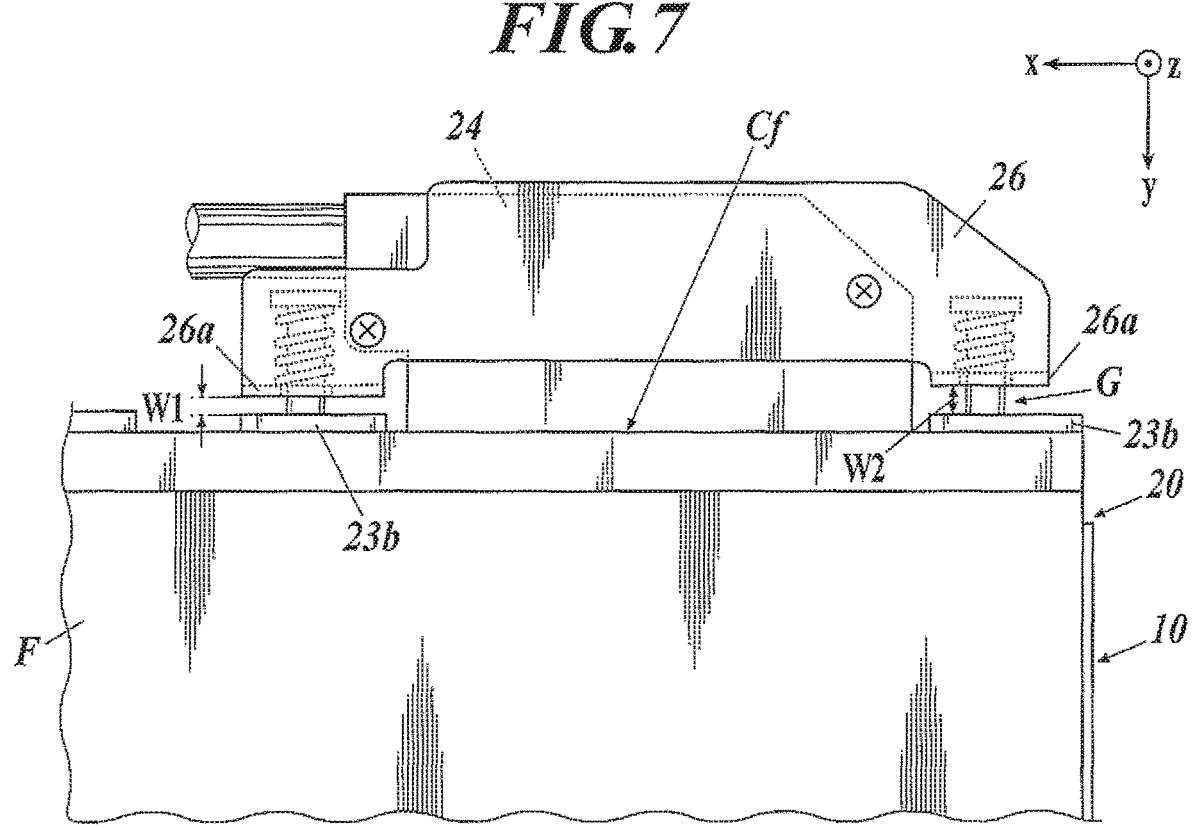
FIG. 7 is a plan view of a connector and a retainer according to Modification 1.

Alternatively, as illustrated in FIG. 7, for example, the retainer 26 may be preliminarily formed in a shape such that the width W1 (or shift distance W1) of the gap G defined between one of the bent portions 26a of the retainer 26 and the corresponding retention tab 23b is smaller than the width W2 (or shift distance W2) of the gap G defined between the other bent portion 26a of the retainer 26 and the corresponding retention tab 23b, after the loading of the radiation image capturing apparatus F on the retention section 20 of the cassette holder 10.

Like the configurations described above (shown in FIGS. 6A and 6B), such a configuration allows one end of the connector 24 to be detached from the connection port Cf of the radiation image capturing apparatus F earlier than the other end of the connector 24, when the loaded radiation image capturing apparatus F is drawn frontward to be detached from the cassette holder 10. Accordingly, the connection port Cf of the radiation image capturing apparatus F can be appropriately and readily disconnected from the connector 24 of the capturing platform 1 when the radiation image capturing apparatus F is detached from the capturing platform 1.

Modification 1, which includes the retainer 26 having a shape different from that in the embodiments described above, can achieve the same advantageous effects as the embodiments described above, without the regulator 30. In other words, Modification 1 advantageously eliminates the need for the regulator 30.

<Modification 2 of Connector and Retainer>

In the embodiments and Modification 1 described above, the regulator 30 (in the embodiments) or the retainer 26 having a modified shape (Modification 1) contribute to the detachment of one end of the connector 24 from the connection port Cf of the radiation image capturing apparatus F earlier than the other end of the connector 24 when the radiation image capturing apparatus F is drawn. Alternatively, the advantageous effect can be achieved by a connector 24 having a modified shape.

Figure 8A:
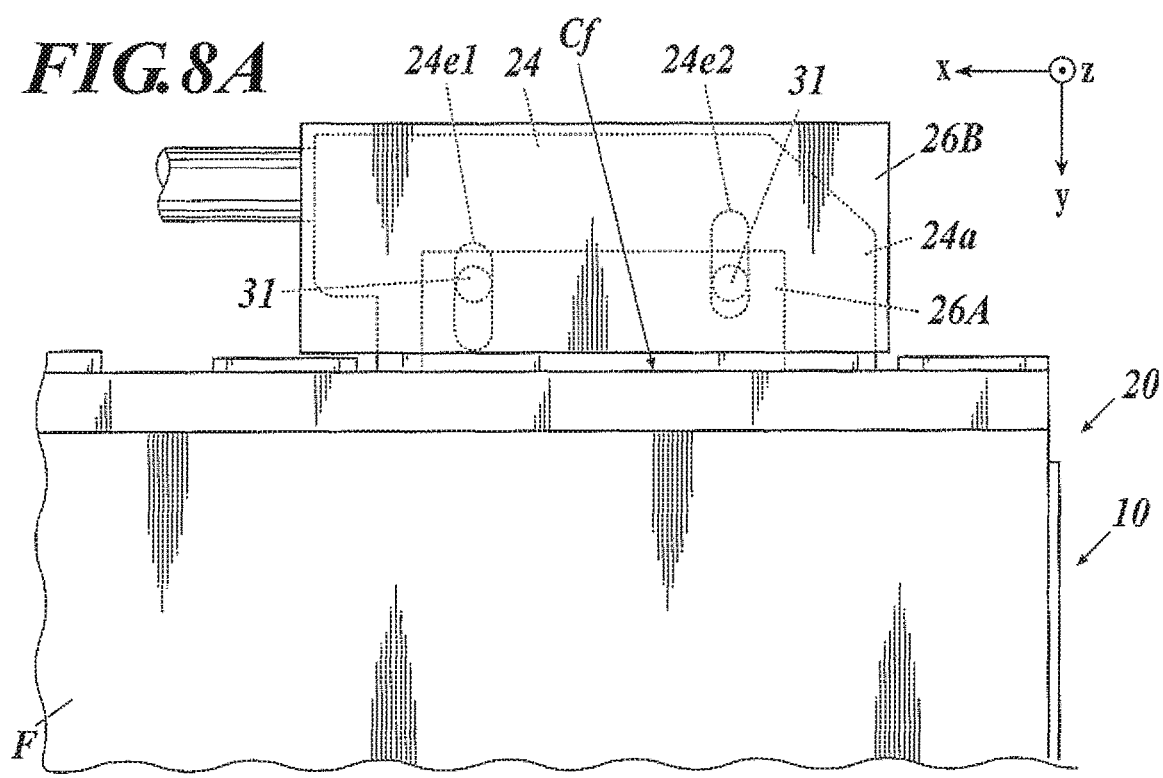
FIG. 8A is a plan view of a connector and retainers according to Modification 2.
Figure 8B:
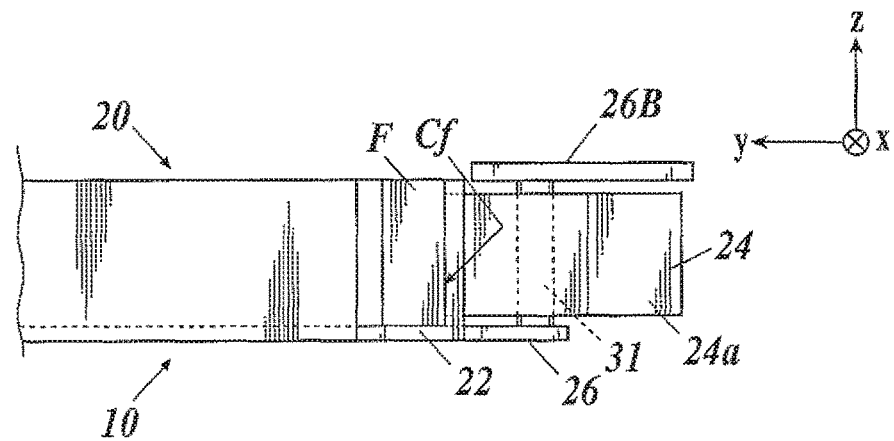
FIG. 8B is a side view of the connector and retainers according to Modification 2.

In detail, as illustrated in FIGS. 8A and 8B, elongated holes 24e1 and 24e2, which extend along y-axis perpendicular to the face provided with the pins 24b (not shown in FIGS. 8A and 8B; refer to FIGS. 4A and 4B), are respectively disposed at two ends of the support 24a of the connector 24. The elongated hole 24e1 of the support 24a is disposed adjacent to the face provided with the pins 24b, and the elongated holes 24e2 of the support 24a are disposed remote from the face provided with the pins 24b.

One of the slide tables 22 adjacent to the cassette holder 10 has a lower retainer 26A configured to hold the connector 24 from the underneath. The lower retainer 26A is provided with two regulating rods 31 protruding upward and respectively disposed at ends of the lower retainer 26A at an equal distance from the end of the slide table 22. The regulating rods 31 are respectively inserted in the elongated holes 24e1 and 24e2 of the connector 24.

In addition, a flat upper retainer 26B is attached to the top end of each regulating rod 31. In the embodiments and Modification 1 described above, the connector 24 and the retainer 26 are moved together with the movement of the drawn radiation image capturing apparatus F. In Modification 2, the lower retainer 26A, the regulating rods 31, and the upper retainer 26B are fixed to the slide table 22 of the cassette holder 10; hence, these components are not moved with the frontward movement of the radiation image capturing apparatus F, and only the connector 24 is moved with the movement of the drawn radiation image capturing apparatus F.

In Modification 2, as illustrated in FIGS. 8A and 8B, predetermined gaps are defined between the connector 24 and the lower retainer 26A and between the connector 24 and the upper retainer 26B. These gaps will be described below.

In Modification 2, as illustrated in FIG. 8A, the configuration described above allows the distance from the rear edge (upper edge in FIG. 8A) of the elongated hole 24e1 at one end of the connector 24 to the corresponding regulating rod 31 to be larger than the distance from the rear edge of the elongated hole 24e2 at the other end of the connector 24 to the corresponding regulating rod 31, after the radiation image capturing apparatus F is loaded on the cassette holder 10 and the connection port Cf of the radiation image capturing apparatus F is connected to the connector 24 of the cassette holder 10.

Accordingly, only the connector 24 is moved frontward with the movement of the connection port Cf of the radiation image capturing apparatus F, when the radiation image capturing apparatus F is drawn frontward to be detached from the cassette holder 10. During the frontward (downward in FIG. 8A) movement of the connector 24, the rear edge of the elongated hole 24e1 at one end of the connector 24 immediately comes into contact with the corresponding regulating rod 31, reducing the shift distance of the one end of the connector 24.

In contrast, the other end of the connector 24 moves in a shift distance larger than that of the one end of the connector 24, since the distance between the rear edge of the elongated hole 24e2 and the corresponding regulating rod 31 are larger than the distance between the rear edge of the elongated hole 24e1 and the corresponding regulating rod 31. Accordingly, the other end of the connector 24 is moved frontward beyond the one end of the connector 24 with the movement of the radiation image capturing apparatus F.

Such a configuration in Modification 2 allows one end of the connector 24 to be detached from the connection port Cf of the radiation image capturing apparatus F earlier than the other end of the connector 24, when the loaded radiation image capturing apparatus F is drawn frontward to be detached from the cassette holder 10. Accordingly, the connection between the connection port Cf of the radiation image capturing apparatus F can be appropriately and readily disconnected from the connector 24 of the capturing platform 1, when the radiation image capturing apparatus F is detached from the capturing platform 1.

<Urging Connector toward Cassette Holder>

In the embodiments and Modification 1 described above, the guide rods 28 are respectively inserted in the holes 26h (refer to FIGS. 5A and 5B) in the bent portion 26a. The guide rods 28 guide the frontward movement and the rearward movement (along y-axis) of the connector 24 and the ends of the retainer 26. The guide rod 28 also locks the connector 24 and the retainer 26 such that the connector 24 and the retainer 26 are not detached from the retention section 20 of the cassette holder 10 while the radiation image capturing apparatus F is not loaded on the cassette holder 10.

As described above, upon detachment of the radiation image capturing apparatus F from the cassette holder 10, the connector 24 magnetically fixed to the connection port Cf of the radiation image capturing apparatus F and the retainer 26 are automatically moved with the movement of the drawn radiation image capturing apparatus F, without urge of the connector 24 toward the retention section 20 of the cassette holder 10. Accordingly, the connector 24 and the retainer 26 are not necessarily urged toward the retention section 20 of the cassette holder 10, for the purpose or advantageous effects of detaching one end of the connector 24 from the connection port Cf of the radiation image capturing apparatus F earlier than the other end of the connector 24 to facilitate the detachment of the connector 24 from the connection port Cf of the radiation image capturing apparatus F.

Figure 9:
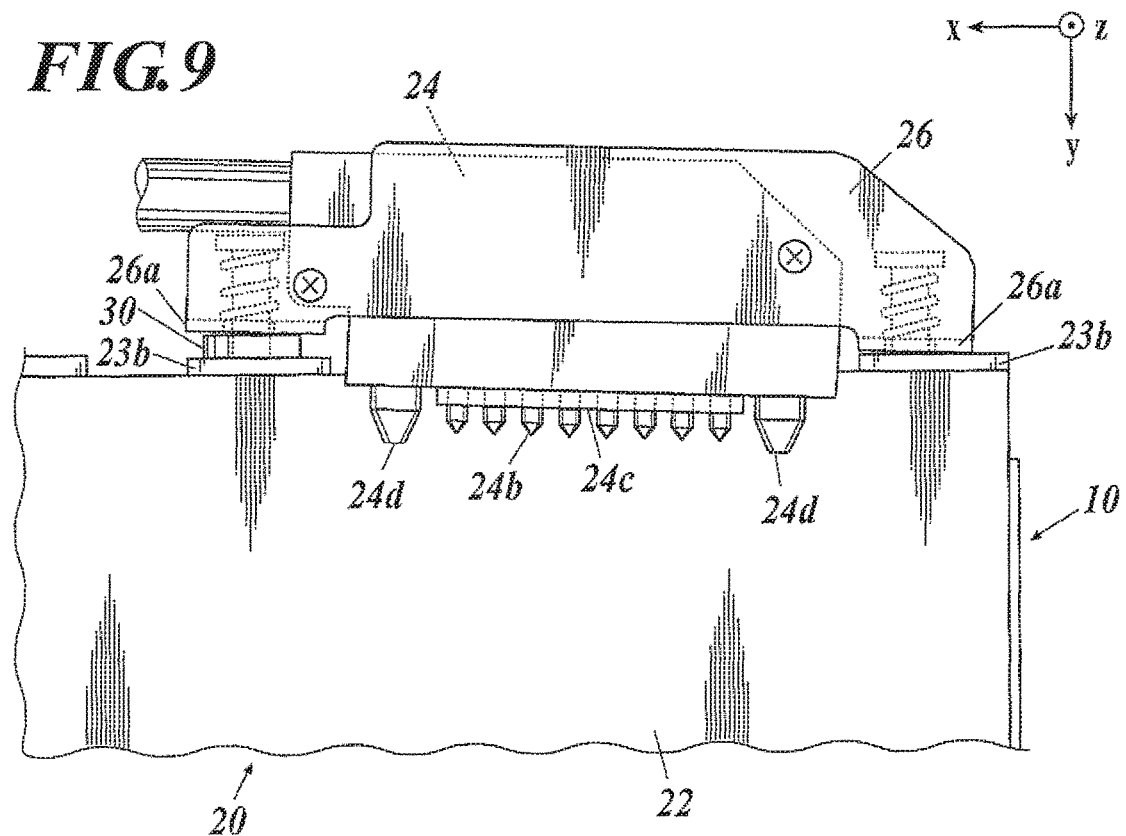
FIG. 9 illustrates the connector protruding beyond retention tabs toward the inside of the retention section of the cassette holder on which the radiation image capturing apparatus is not loaded.

The embodiments described above, however, include the springs 29 to urge the connector 24 toward the retention section 20 (to hold the radiation image capturing apparatus F) of the cassette holder 10 along the y-axis. As illustrated in FIG. 9, the face provided with the pins 24b of the connector 24 protrudes beyond the retention tabs 23b toward the inside of the retention section 20, while the radiation image capturing apparatus F is not loaded on the cassette holder 10.

Although the springs are not depicted in Modification 2 in FIGS. 8A and 8B, Modification 2 may also include the springs to urge the connector 24 toward the retention section 20 (to hold the radiation image capturing apparatus F) of the cassette holder 10. Such a configuration allows the face of the connector 24 provided with the pins 24b to protrude beyond the retention tabs 23 toward the inside of the retention section 20, while the radiation image capturing apparatus F is not loaded on the cassette holder 10, like the configuration illustrated in FIG. 9.

<Swaying Movement of Connector>

Figure 10A:
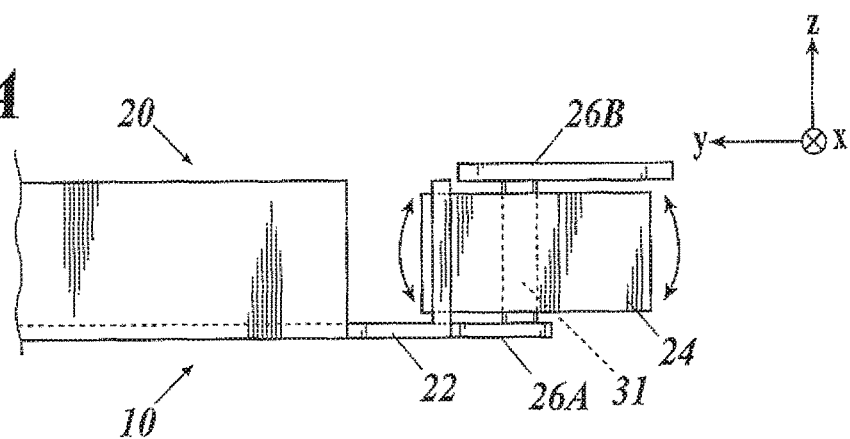
FIG. 10A illustrates the connector according to Modification 2 which is swayable in directions perpendicular to slide tables.

In Modification 2 illustrated in FIGS. 8A and 8B, the connector 24 is held such that predetermined gaps are defined between the connector 24 and the lower retainer 26A and between the connector 24 and the upper retainer 26B. The connector 24 is thus swayable along z-axis perpendicular to the slide tables 22, which functions as the support base of the retention section 20 of the cassette holder 10, within a predetermined angle range, while the radiation image capturing apparatus F is not loaded on the cassette holder 10, as illustrated in FIG. 10A.

Figure 10B:
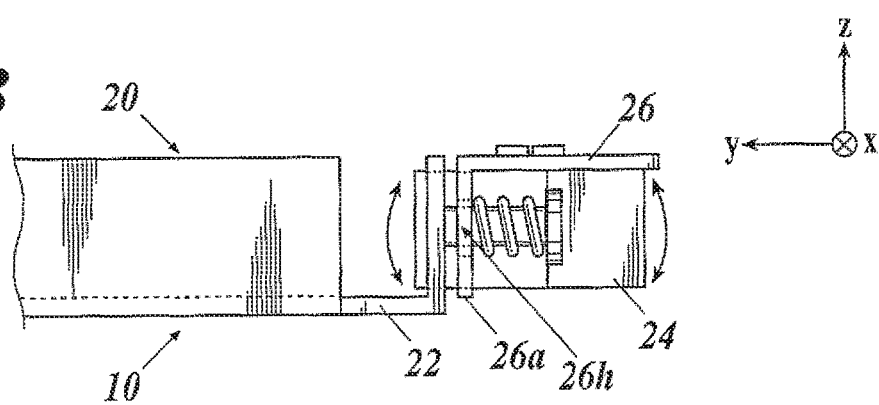
FIG. 10B illustrates the connector according to the embodiment and Modification 1 which is swayable in directions perpendicular to the slide tables.

Also in the embodiments described above and Modification 1, the holes 26h in the bent portions 26a of the retainer 26 may have a larger diameter than the guide rod 28 to be inserted in the holes 26h. Such a configuration allows the connector 24 and the retainer 26 to sway along z-axis perpendicular to the slide tables 22 of the retention section 20 of the cassette holder 10 within a predetermined angle range, while the radiation image capturing apparatus F is not loaded on the cassette holder 10, as illustrated in FIG. 10B.

<Operation of Connector during Loading of Radiation Image Capturing Apparatus>

In the configuration of the connector 24 (and the retainer 26), which is swayable in directions perpendicular to the slide tables 22 while the radiation image capturing apparatus F is not loaded on the cassette holder 10, the connector 24 operates according to the procedure described below, while the radiation image capturing apparatus F is loaded on the cassette holder 10.

Figure 11A:
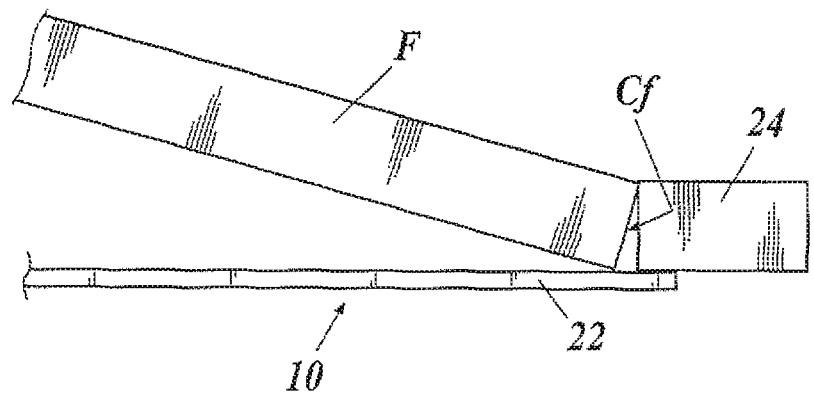
FIG. 11A illustrates the state where a radiation image capturing apparatus to be loaded comes close to the connector.
Figure 11B:
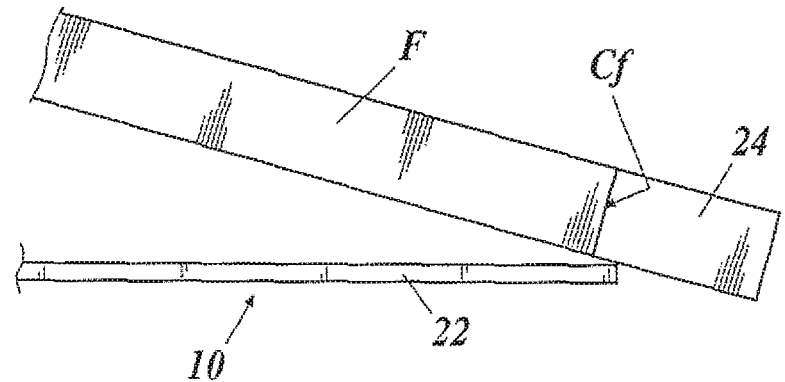
FIG. 11B illustrates the state where the radiation image capturing apparatus is connected to the connector after swaying movement of the connector.

The radiation image capturing apparatus F in a posture slanting relative to the slide tables 22 is loaded on the cassette holder 10 and comes close to the connector 24, as illustrated in FIG. 11A; then, the connector 24 sways in directions perpendicular to the slide tables 22, slants relative to the slide tables 22 at an identical angle to the radiation image capturing apparatus F, and is then automatically connected to the connection port Cf of the radiation image capturing apparatus F (i.e., without manual connection of the connection port Cf of the radiation image capturing apparatus F to the connector 24 by a radiological technologist), as illustrated in FIG. 11B.

The radiation image capturing apparatus F connected to the connector 24 is then laid parallel to the slide tables 22 of the cassette holder 10 to be held by the retention tabs 23 of the retention section 20. Such an operation enables loading of the radiation image capturing apparatus F on the cassette holder 10 and appropriate automatic connection of the connection port Cf of the radiation image capturing apparatus F to the connector 24 of the cassette holder 10 at the same time (refer to FIGS. 5A, 5B, 7, 8A, and 8B).

FIGS. 11A and 11B schematically illustrate the connection of the connection port Cf of the loaded radiation image capturing apparatus F to the connector 24, and the retention tabs 23 and any other component of the cassette holder 10 are not depicted in the drawings.

In the embodiments and Modifications 1 and 2 described above, the connector 24 is swayable in directions perpendicular to the slide tables 22, which function as the support base of the cassette holder 10. Even if the radiation image capturing apparatus F in a posture slanting relative to the slide tables 22 is loaded on the cassette holder 10, the connector 24 sways in the directions perpendicular to the slide tables 22 to be appropriately and automatically (i.e., readily) connected to the connection port Cf of the radiation image capturing apparatus F.

When the radiation image capturing apparatus F is detached from the cassette holder 10, one end of the connector 24 can be detached from the connection port Cf of the radiation image capturing apparatus F earlier than the other end of the connector 24, as described above. The connection port Cf of the radiation image capturing apparatus F is thereby appropriately and readily disconnected from the connector 24 of the capturing platform 1.

Accordingly, the connector 24 of the capturing platform 1 according to the embodiments and Modifications 1 and 2, which is swayable in the directions perpendicular to the slide tables 22 functioning as the support base of the cassette holder 10, can appropriately and readily connect and disconnect to/from the connection port Cf of the radiation image capturing apparatus F, upon the attachment and the detachment of the radiation image capturing apparatus F to/from the cassette holder 10.

<Openable Slide Tables>

In the embodiments described above, the two slide tables 22 are provided on the upper side of the turn table 21 (refer to FIG. 2) of the cassette holder 10. The two slide tables 22 are openable in opposite directions parallel to the turn table 21.

While the two slide tables 22 are being closed, the retention section 20 of the cassette holder 10 can be loaded with a 14-by-17-inch radiation image capturing apparatus F, for example. While the slide tables 22 are being opened, the retention section 20 of the cassette holder 10 can be loaded with a 17-by-17 inch radiation image capturing apparatus F.

In the embodiments described above, the cassette holder 10, which is provided with the movable slide tables 22, can be loaded with radiation image capturing apparatuses F of different sizes, for example, one with a square planar profile with four sides having an equal length (17-by-17 inches, for example) and the other with a rectangular planar profile with two pairs of sides having different lengths (14-by-17 inches, for example) perpendicular to each other.

Such a cassette holder 10 eliminates the need for preparation of cassette holders for radiation image capturing apparatus F of different sizes. The cassette holder 10, which is provided with the movable two slide tables 22, can be loaded with various radiation image capturing apparatuses F of different sizes.

In the embodiment, the slide tables 22 are configured to move apart from each other in opposite directions at an equal distance over the turn table 21. As illustrated in FIG. 2, a stopper 32 is provided on the turn table 21 of the cassette holder 10. The stopper 32 is extendable and retractable from/in the turn table 21, in this embodiment.

For example, before loading of a 14-by-17-inch radiation image capturing apparatus F on the cassette holder 10, the stopper 32 is extended upward to engage with one of the slide tables 22 to prevent the opening movement of the slide tables 22. The 14-by-17-inch radiation image capturing apparatus F is then loaded on the cassette holder 10.

For example, before loading of a 17-by-17-inch radiation image capturing apparatus F on the cassette holder 10, the stopper 32 is retracted downward to release the engagement with the slide table 22 and the slide tables 22 are moved to be opened. The 17-by-17-inch radiation image capturing apparatus F is then loaded on the cassette holder 10.

In this embodiment, the slide tables 22 are configured to move apart from each other in opposite directions at an equal distance over the turn table 21, as described above; hence, the center position (defined between x-axis and y-axis) between the slide tables 22 remains unchanged regardless of the open or closed state of the slide tables 22.

Figure 12A:
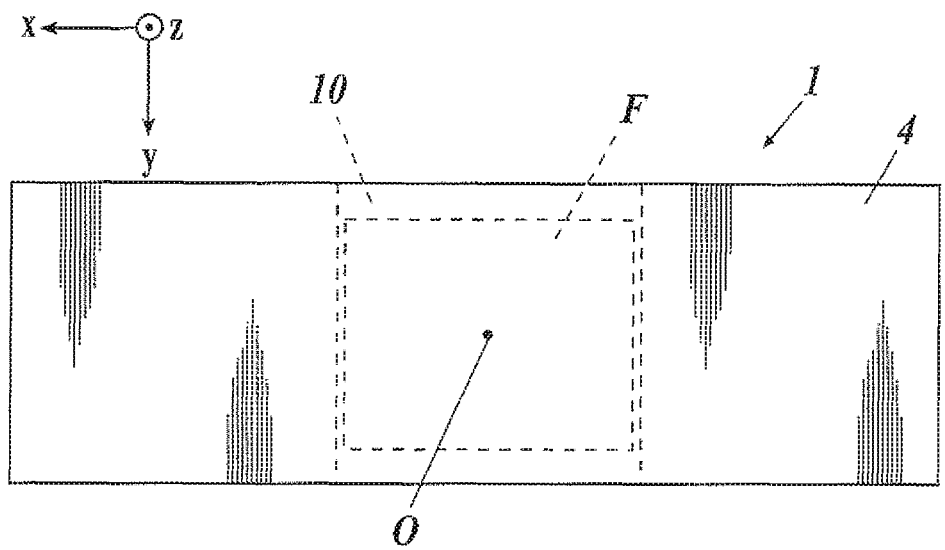
FIG. 12A is a plan view of the radiation image capturing apparatus disposed in a vertical orientation and loaded on the cassette holder of the capturing platform.
Figure 12B:
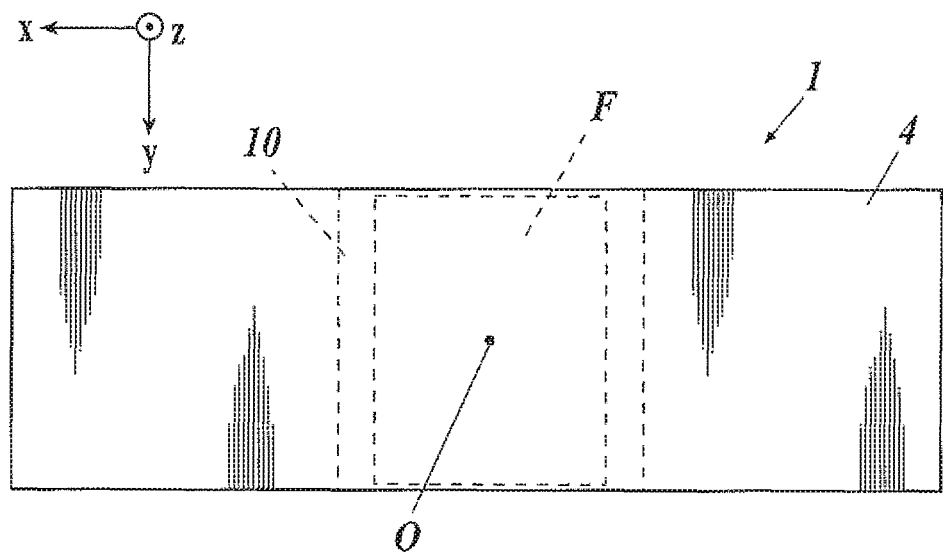
FIG. 12B is a plan view of the radiation image capturing apparatus disposed in a horizontal orientation and loaded on the cassette holder of the capturing platform.

Accordingly, the cassette holder 10 of the embodiment, which is provided with the movable slide tables 22, can be loaded with any radiation image capturing apparatus F of different sizes such that the central position of the radiation image capturing apparatus F is always disposed at an identical position (refer to the central position O of the radiation image capturing apparatus F illustrated in FIGS. 12A and 12B described below).

Since the cassette holder 10 of the embodiment is configured to be loaded with radiation image capturing apparatus F of two different sizes (14-by-17 inches and 17-by-17 inches, for example), the two slide tables 22 are configured to move only along the y-axis.

Alternatively, four slide tables 22 may be provided which are movable along not only in the y-axis direction but also in the x-axis direction perpendicular to the y-axis direction so that the cassette holder 10 can be loaded with radiation image capturing apparatuses F of more different sizes.

Furthermore, in the embodiments and Modifications 1 and 2 described above, the connector 24 is configured to engage with the guide rods 28 (refer to FIGS. 5A and 5B) protruding from the respective retention tabs 23b fixed to the slide table 22, or is configured to engage with the regulating rods 31 (refer to FIGS. 8A and 8B) protruding upward from the lower retainer 26A of the slide table 22. Since the connector 24 is movable together with the movement of the slide tables 22, the positioning relations between the connector 24 and slide tables 22 and between the connector 24 and the retention tabs 23b remain unchanged, regardless of the open or closed state of the slide tables 22 over the turn table 21.

Accordingly, the slide tables 22, which are movable over the turn table 21, do not hinder but appropriately provide the advantageous functional effects inherent in the present invention, upon the removal of the radiation image capturing apparatus F from the cassette holder 10 and the loading of the radiation image capturing apparatus F on the cassette holder 10.

<Retention Section Entirely Turnable>

In the embodiments described above, the turn table 21 functioning as the support base of the retention section 20 of the cassette holder 10 is turnably attached to the tray 12 (refer to FIG. 2). Turning of the turn table 21 relative to the tray 12 can turn the entire retention section 20 of the cassette holder 10.

The cassette holder 10 having such a configuration can be loaded with the radiation image capturing apparatus F in two different orientations. For example, a 14-by-17-inch radiation image capturing apparatus F may be loaded in a vertical orientation on the cassette holder 10 (i.e., the radiation image capturing apparatus F may be disposed on the cassette holder 10 such that the longitudinal sides extend in the x-axis), as illustrated in FIG. 12A, and the radiation image capturing apparatus F may be loaded in a horizontal orientation on the cassette holder 10 (i.e., the radiation image capturing apparatus F may be disposed on the cassette holder 10 such that the longitudinal sides extend along the y-axis), as illustrated in FIG. 12B.

Although not illustrated, the turn table 21 of the cassette holder 10 is generally turnable by 90 degrees relative to the tray 12 such that the radiation image capturing apparatus F may be loaded in both the vertical orientation (refer to FIG. 12A) and the horizontal orientation (refer to FIG. 12B) relative to the capturing platform 1.

For the radiation image capturing apparatus F with a square planar profile with four sides having an equal length (17-by-17 inches, for example), an image captured with the radiation image capturing apparatus F in the vertical orientation is the same as an image captured with the radiation image capturing apparatus F in the horizontal orientation. The image captured with the radiation image capturing apparatus F in the horizontal orientation may require an additional image processing operation to rotate the image by 90 degrees into the vertical orientation.

Accordingly, before the loading of the radiation image capturing apparatus F having a square planar profile with four sides having an equal length (17-by-17 inches, for example) on the cassette holder 10, the turn table 21 may be prevented from turning relative to the tray 12.

In detail, before the loading of the radiation image capturing apparatus F with a rectangular planar profile with two pairs of sides having different lengths (for example, 14-by-17 inches, hereinafter simply referred to as rectangular radiation image capturing apparatus F) on the cassette holder 10, the turn table 21 can turn relative to the tray 12, so that the radiation image capturing apparatus F can turn on the plane on which the radiation image capturing apparatus F lies (i.e., the plane parallel to the tray 12).

In contrast, before the loading of radiation image capturing apparatus F having a planar profile with four sides having an equal length (for example, 17 by 17 inches, hereinafter simply referred as square radiation image capturing apparatus F) on the cassette holder 10, the turn table 21 does not turn relative to the tray 12, so that the radiation image capturing apparatus F is prevented from turning.

The cassette holder 10 having such a configuration can be loaded with the rectangular radiation image capturing apparatus F both in a vertical orientation and in a horizontal orientation, enabling appropriate image capturing in vertical and horizontal directions. In addition, the cassette holder 10 is loaded with the square radiation image capturing apparatus F such that the radiation image capturing apparatus F is prevented from turning, appropriately eliminating the need for additional image processing operations to rotate an image captured with the radiation image capturing apparatus F by 90 degrees.

For example, the cassette holder 10, which can be loaded with the rectangular radiation image capturing apparatus F such that the turn table 21 can turn relative to the tray 12 and can be loaded with the square radiation image capturing apparatus F such that the turn table 21 does not turn relative to the tray 12, may have a specific configuration as follows.

Figure 13A:
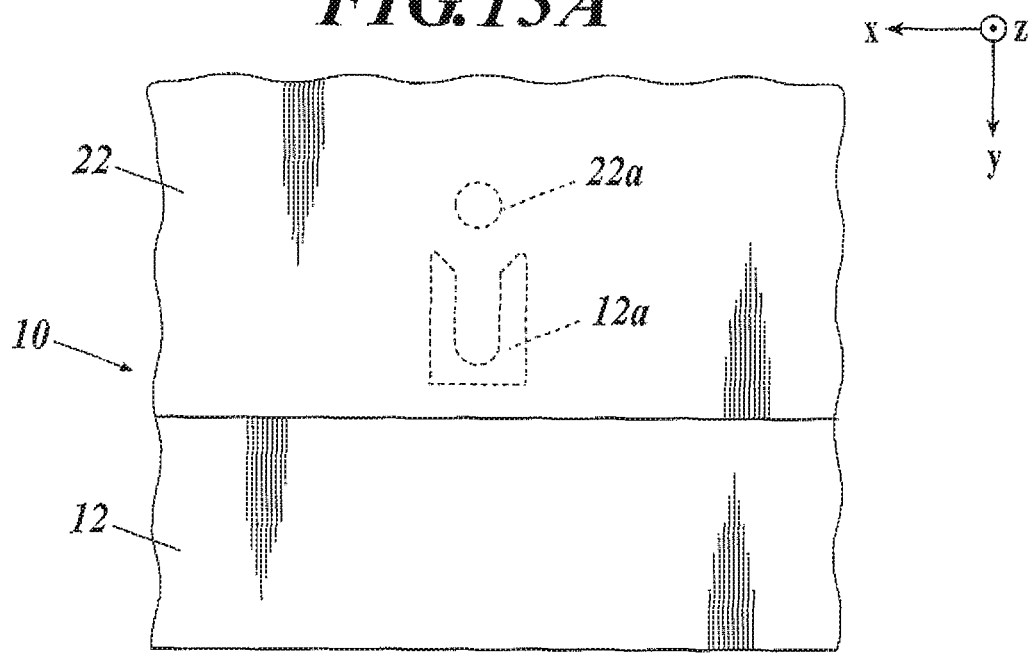
FIG. 13A is a plan view of a protrusion provided on the slide table and an engaging member provided on the tray.

With reference to FIG. 13A, for example, a protrusion 22a is provided on the bottom face of one of the slide tables 22

(or on each of the bottom faces of the two slide tables 22) and extends toward the tray 12 behind the slide tables 22. In addition, an engaging member 12a is provided on the upper side of the tray 12. After the slide table 22 is opened in a vertical direction (i.e., along y-axis illustrated in FIG. 2) with the movement of the protrusion 22a along y-axis, the engaging member 12a engages with the protrusion 22a.

Such a configuration allows the slide tables 22 to turn, while the slide tables 22 are being closed (i.e., in the state to be loaded with the rectangular radiation image capturing apparatus F; refer to FIG. 13A) and the protrusion(s) 22a of the slide table(s) 22 is not engaged with the engaging member 12a of the tray 12.

Figure 13B:
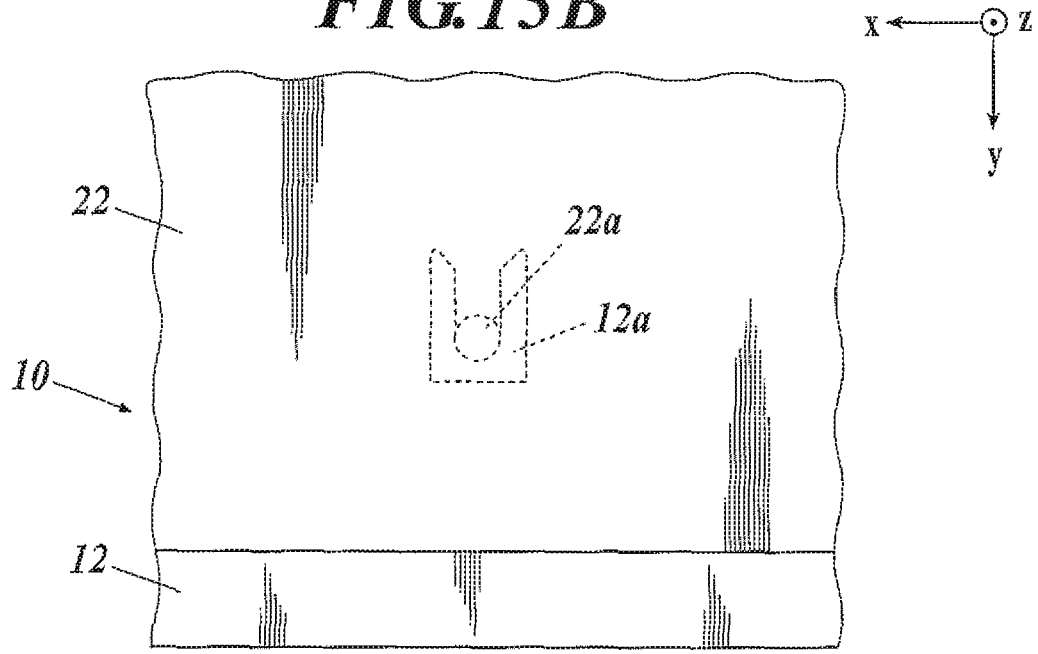
FIG. 13B is a plan view of the engaging member engaging with the protrusion on the slide table opened.

In contrast, such a configuration prevents the slide tables 22 from turning, while the slide tables 22 are being opened (i.e., in the state to be loaded with the square radiation image capturing apparatus F; refer to FIG. 13B) and the protrusion(s) 22a of the slide table(s) 22 is engaged with the engaging member 12a of the tray 12 after moving with the opening movement of the slide table 22.

Accordingly, the cassette holder 10 having the configuration described above can be loaded with the rectangular radiation image capturing apparatus F such that the turn table 21 can turn relative to the tray 12, and the square radiation image capturing apparatus F such that the turn table 21 cannot turn relative to the tray 12.

It should be noted that even after the cassette holder 10 is loaded with the rectangular radiation image capturing apparatus F such that the turn table 21 and the slide tables 22 can turn relative to the tray 12, the relative positioning relations between the connector 24 and the slide tables 22 and between the connector 24 and the retention tabs 23b remain unchanged because the connector 24 moves together with the slide tables 22.

Accordingly, according to the configuration such that the turn table 21 and the slide tables 22 can turn relative to the tray 12, such configuration does not hinder but appropriately provides the advantageous functional effects inherent in the present invention upon the detachment of the radiation image capturing apparatus F from the cassette holder 10 and the loading of the radiation image capturing apparatus on the cassette holder 10.

<Embodiments of Mobile Radiation Capturing Apparatus and Portable Radiation Capturing Apparatus>

Figure 15:
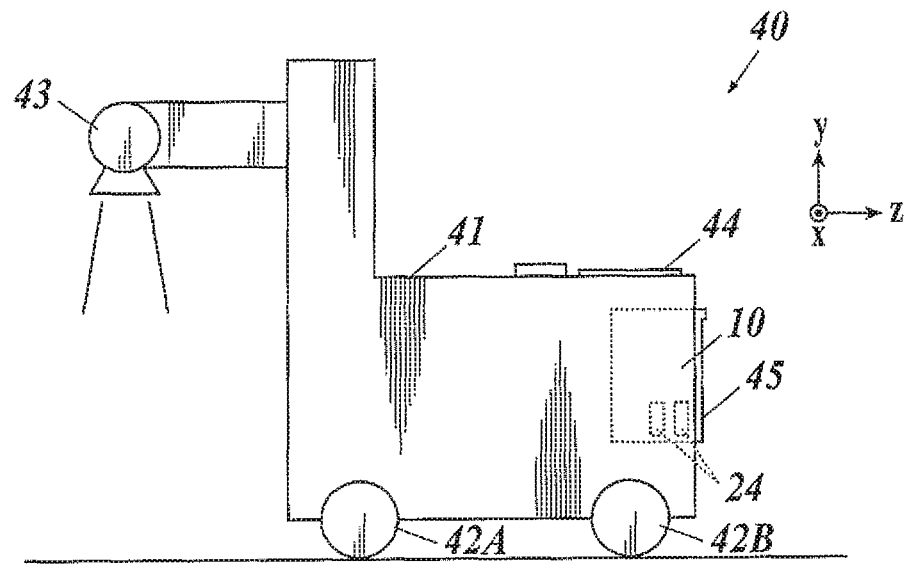
FIG. 15 is a schematic view of a mobile radiation capturing apparatus according to an embodiment.
Figure 16:
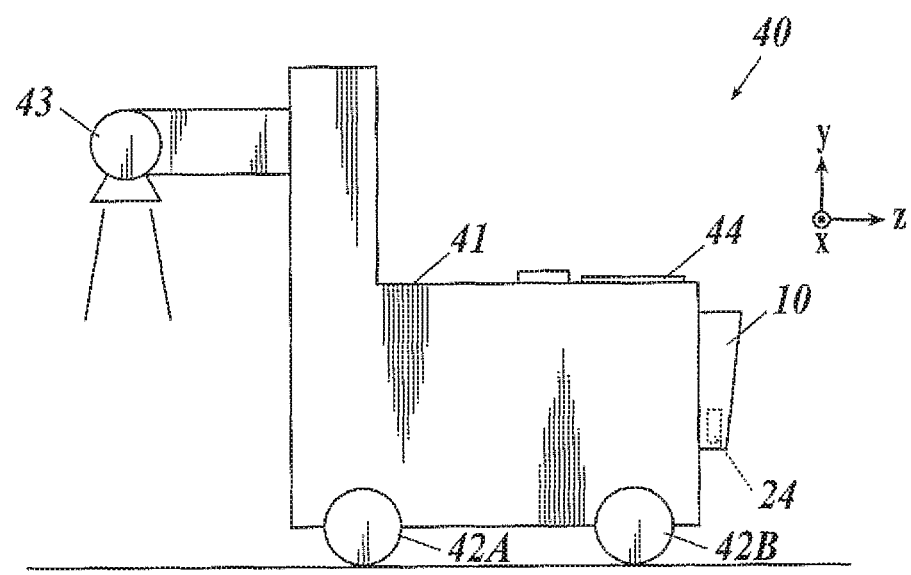
FIG. 16 is a schematic view of a mobile radiation capturing apparatus provided with a cassette holder having a shape according to a modification.
Figure 17:
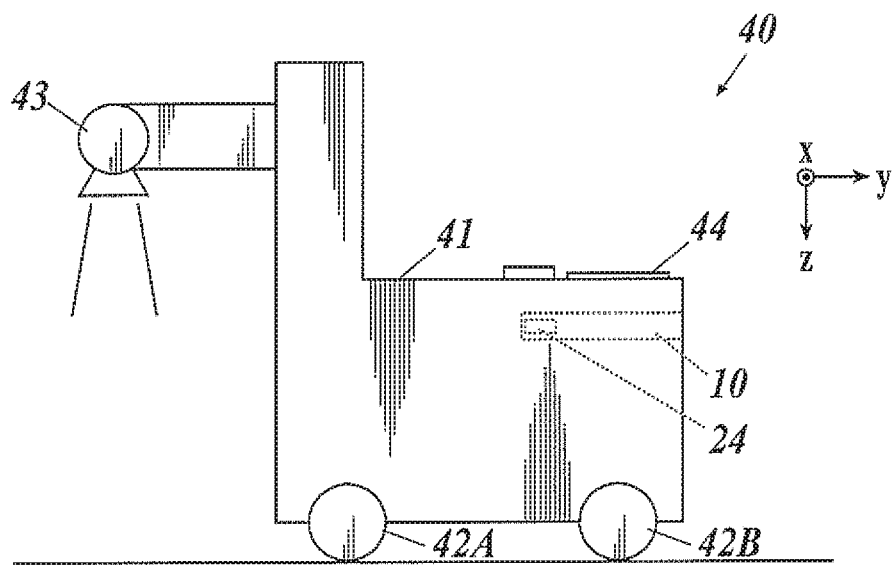
FIG. 17 is a schematic view of a mobile radiation capturing apparatus provided with a cassette holder having a shape according to another modification.

FIG. 15 is a schematic view of an exemplary mobile radiation capturing apparatus 40 according to an embodiment of the present invention. The illustrations of a retainer 26 and any other component disposed in the cassette holder 10 are not depicted in FIG. 15 (the same is applied to FIGS. 16 to 20B).

The mobile radiation capturing apparatus 40 is moved to a medical ward accommodating a patient and is used to capture radiographic images of the patient (subject). For the radiographic image capturing, the mobile radiation capturing apparatus 40 is used together with the radiation image capturing apparatus F.

A body 41 of the mobile radiation capturing apparatus 40 is mainly composed of wheels 42A and 42B, a radiation illuminator 43, an operational display 44, a door 45, and a cassette holder 10.

The wheels 42A and 42B, functioning as a moving mechanism, are attached to a lower portion of the body 41, and are electrically or manually rotated to move the mobile radiation capturing apparatus 40 between medical wards accommodating patients.

The radiation illuminator 43 disposed at an upper portion of the body 41 emits radiation rays toward a patient in response to an operation on the operational display 44 by a radiological technologist. The radiation illuminator 43 is adjustable in position, such as height and tilt, depending on the purpose of the image capturing. Like the emission of radiation rays, the position of the radiation illuminator 43 is adjusted in response to an operation on the operational display 44 by the radiological technologist or is directly adjusted by manual operation of the radiological technologist.

While the mobile radiation capturing apparatus 40 is being moved, the radiation image capturing apparatus F is accommodated in the cassette holder 10. Before radiographic image capturing, the radiation image capturing apparatus F is detached from the cassette holder 10, and is disposed between the region of interest (region to be captured) of a patient and a bed (not shown).

The door 45 disposed on a side of the body 41 is openable in a swinging or sliding manner. To insert the radiation image capturing apparatus F in the cassette holder 10, an operator swings or slides the door 45 and then inserts a cassette in the cassette holder 10 through an insertion slot formed at an upper portion of the cassette holder. After the insertion of the radiation image capturing apparatus F into the cassette holder 10, the operator revolves or slides the door 45 again to close the insertion slot.

A connector 24 and a retainer (26) are disposed at a far side of the cassette holder 10 in the inserting direction. The connector 24 is held by the retainer (26) so as to be swayable in directions perpendicular to the inserting direction of the radiation image capturing apparatus F. Accordingly, the radiation image capturing apparatus F is automatically connected to the connector 24 when inserted in the cassette holder 10, like the case of the capturing platform described above.

When the radiation image capturing apparatus F is detached from the cassette holder 10, one end of the connector 24 is detached from the connection port Cf (not shown) of the radiation image capturing apparatus F earlier than the other end of the connector 24, due to the difference in shift distance between the one end of the connector 24 in the drawing direction of the radiation image capturing apparatus F and the other end of the connector 24, like the case of the capturing platform described above.

In a modification of the embodiments described above, as illustrated in FIG. 16, the cassette holder 10 may be free from the swinging or sliding door 45. Also in this modification, the connector 24 and the retainer (26) are disposed in the far side of the cassette holder 10, and the connector 24 is held by the retainer (26) so as to be swayable in directions perpendicular to the inserting direction of the radiation image capturing apparatus F, as described above. Accordingly, the radiation image capturing apparatus F is automatically connected to the connector 24 when inserted in the cassette holder 10.

When the radiation image capturing apparatus F is detached from the cassette holder 10, one end of the connector 24 is detached from the connection port Cf (not shown) of the radiation image capturing apparatus F earlier than the other end of the connector 24, due to the difference in shift distance between the one end of the connector 24 in the drawing direction of the radiation image capturing apparatus F and the other end of the connector 24, like the case of the capturing platform described above.

In another modification of the embodiments described above, as illustrated in FIG. 17, the cassette holder 10 may be disposed in the body 41, and the radiation image capturing apparatus F may be inserted in a horizontal direction or an oblique direction.

Also in this modification, the connector 24 and the retainer (26) are disposed in the far side of the inserting direction of the cassette holder 10, and the connector 24 is held by the retainer (26) so as to be swayable in directions perpendicular to the inserting direction of the radiation image capturing apparatus F, as described above. Accordingly, the radiation image capturing apparatus F is connected to the connector 24 when inserted in the cassette holder 10.

When the radiation image capturing apparatus F is detached from the cassette holder 10, one end of the connector 24 is detached from the connection port Cf (not shown) of the radiation image capturing apparatus F earlier than the other end of the connector 24, due to the difference in shift distance between the one end of the connector 24 in the drawing direction of the radiation image capturing apparatus F and the other end of the connector 24, like the case of the capturing platform described above.

Figure 18:
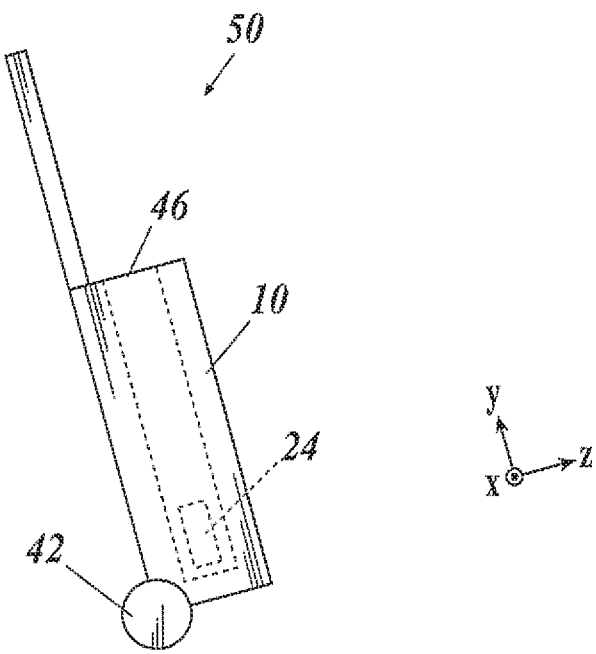
FIG. 18 is a schematic view of a mobile cassette holder according to an embodiment.

FIG. 18 is a schematic view of a mobile cassette holder 50 according to an embodiment of the present invention.

The mobile cassette holder 50 is composed of a cassette holder 10, wheels 42 as a moving mechanism, and a grip 47. For the portable use of the cassette holder 50, the radiation image capturing apparatus F can be accommodated in the cassette holder 10.

The connector 24 and the retainer (26) are disposed in the far side of the cassette holder 10 in the inserting direction, and the connector 24 is held by the retainer (26) so as to be swayable in directions perpendicular to the inserting direction of the radiation image capturing apparatus F, as described above. Accordingly, similar to the mobile radiation image capturing apparatus, the radiation image capturing apparatus F is connected to the connector 24 when inserted in the cassette holder 10.

When the radiation image capturing apparatus F is detached from the cassette holder 10, one end of the connector 24 is detached from the connection port Cf (not shown) of the radiation image capturing apparatus F earlier than the other end of the connector 24, due to the difference in shift distance between the one end of the connector 24 in the drawing direction of the radiation image capturing apparatus F and that of the other end of the connector 24, like the case of the capturing platform described above.

Figure 19A:
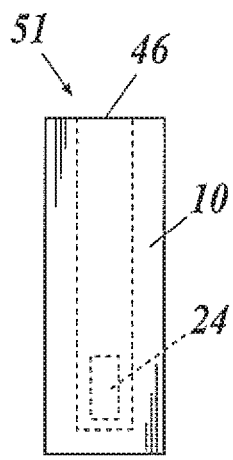
FIG. 19A is a schematic side view of a portable cassette holder according to an embodiment.
Figure 19B:
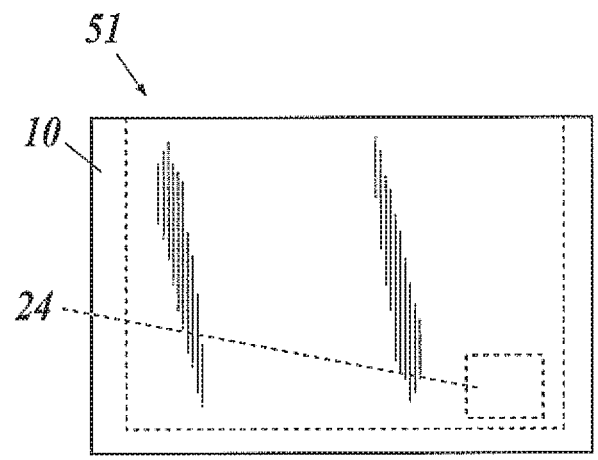
FIG. 19B is a plan view of the portable cassette holder illustrated in FIG. 19A.

FIGS. 19A and 19B are schematic views of a portable cassette holder 51 being a portable cassette holder 10 according to a modification of the embodiments described above in which only the cassette holder 10 is portable. In the portable cassette holder 51, the connector 24 and the retainer (26) are disposed in the far side of the cassette holder 10 in the inserting direction, and the connector 24 is held by the retainer (26) so as to be swayable in directions perpendicular to the inserting direction of the radiation image capturing apparatus F. Accordingly, the radiation image capturing apparatus F is connected to the connector 24 when inserted in the cassette holder 10, like the case of the portable cassette holder described above.

When the radiation image capturing apparatus F is detached from the cassette holder 10, one end of the connector 24 is detached from the connection port Cf (not shown) of the radiation image capturing apparatus F earlier than the other end of the connector 24, due to the difference in shift distance between the one end of the connector 24 in the drawing direction of the radiation image capturing apparatus F and that of the other end of the connector 24, like the case of the capturing platform described above.

In FIGS. 15, 16, 18, 19A, and 19B described above, a larger cassette insertion slot 46 of the cassette holder 10 allows clumsy operation to insert the radiation image capturing apparatus F in the cassette insertion slot 46, leading to high operability during the insertion of the radiation image capturing apparatus F. To ensure the connection of the radiation image capturing apparatus F to the connector 24 disposed on the far side of the cassette holder 10 in the inserting direction, the position of the radiation image capturing apparatus F in the cassette holder 10 should preferably be regulated to an extent.

Figure 20A:
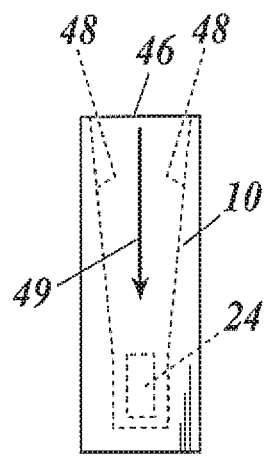
FIG. 20A is a side view of a cassette holder having a shape according to a modification.
Figure 20B:
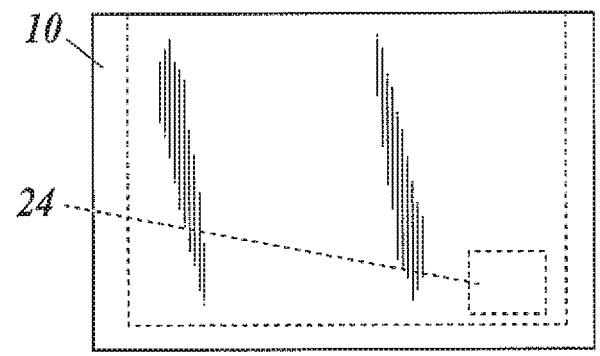
FIG. 20B is a plan view of the cassette holder illustrated in FIG. 20A.

Accordingly, with reference to FIG. 20A, the cassette holder 10 has a tilting side wall 48 extending from the cassette insertion slot 46 toward the connector 24 at the far side of the cassette holder 10. The radiation image capturing apparatus F to be inserted comes into contact with the tilting side wall and moves along the wall. Such a configuration enhances the operability of the insertion of the radiation image capturing apparatus F and ensures the connection of the radiation image capturing apparatus F to the connector 24. A side wall having larger tilting angles may result in a failure of the connection and an oversized cassette holder 10. The side wall 48 thus preferably tilts at an angle of 2 degrees to 40 degrees from the inserting direction 49 of the radiation image capturing apparatus F.

It is understood that the embodiments described above should not be construed to limit the present invention and may be appropriately modified without departing from the scope of the present invention.

In the description above, the capturing platform 1 is designed for supine radiography. A capturing platform 1 for standing radiography includes, for example, retention tabs 23 having a C-shaped cross-section, in place of retention tabs 23 having a plate shape, to prevent the radiation image capturing apparatus F from dropping from the cassette holder 10, as appropriate.

The embodiments and variations of the present invention disclosed herein should be considered to be mere examples and not limitative in all respects. The scope of the present invention is defined not by the above descriptions but by the claims, and is intended to cover all the modifications having equivalent meanings to those of the claims or being within the scope of the claims.

The invention claimed is:

1. A cassette holder capable of being loaded with a radiation image capturing apparatus including a housing, a two-dimensional array of radiation detecting elements accommodated in the housing, and a connection port, the cassette holder comprising:

retention tabs to hold the radiation image capturing apparatus loaded on the cassette holder; and a connector connectable to the connection port of the radiation image capturing apparatus held by the retention tabs, wherein when the connector is connected to the connection port, the connector is magnetically fixed to the connection port, when the radiation image capturing apparatus is drawn to be detached from the cassette holder, the connector is movable with movement of the connection port magnetically fixed to the connector, and the movement of the connector moved with the connection port is regulated such that a shift distance of one end of the connector is smaller than a shift distance of the other end of the connector, and thereby the one end of the connector is detached from the connection port of the radiation image capturing apparatus earlier than the other end of the connector.

2. The cassette holder according to claim 1, wherein the connector is fixed to a retainer, and
when the radiation image capturing apparatus is drawn to be detached from the cassette holder, the movements of the retainer and the connector are regulated such that the shift distance of one end of the retainer is smaller than the shift distance of the other end of the retainer, and thereby the one end of the connector is detached from the connection port of the radiation image capturing apparatus earlier than the other end of the connector, wherein the retainer moves together with the connector moving with the movement of the connection port.

3. The cassette holder according to claim 2, wherein
after the radiation image capturing apparatus is loaded on the cassette holder, gaps are formed between the retainer of the connector and the retention tabs,
while the radiation image capturing apparatus is being detached from the cassette holder, the connector moves with the movement of the connection port, the retainer thereby comes into contact with the retention tabs, and the movements of the retainer and the connector are regulated by the retention tabs, and
the cassette holder further comprises a regulator allowing one of the gaps formed between the one end of the retainer and one of the retention tabs to be smaller than the other gap between the other end of the retainer and the other retention tab, after the radiation image capturing apparatus is loaded on the cassette holder.

4. The cassette holder according to claim 2, wherein
after the radiation image capturing apparatus is loaded on the cassette holder, gaps are formed between the retainer of the connector and the retention tabs,
while the radiation image capturing apparatus is being detached from the cassette holder, the connector moves with the movement of the connection port, the retainer thereby comes into contact with the retention tabs, and the movements of the retainer and the connector are regulated by the retention tabs, and
the retainer is shaped such that one of the gaps formed between the one end of the retainer and one of the retention tabs is smaller than the other gap between the other end of the retainer and the other retention tab, after the radiation image capturing apparatus is loaded on the cassette holder.

5. The cassette holder according to claim 2, wherein
the connector is movably held by the retainer, and
when the radiation image capturing apparatus is drawn to be detached from the cassette holder, the movement of the connector is regulated by the retainer such that the shift distance of the one end of the connector moving is smaller than the shift distance of the other end of the connector, the connector moving with the movement of the connection port.

6. The cassette holder according to claim 1, further comprising:
a support base to hold a rear face of the radiation image capturing apparatus loaded on the cassette holder, wherein
the connector is swayable in directions perpendicular to the support base, and
even if the radiation image capturing apparatus in a posture slanting relative to the support base is loaded on the cassette holder, the connector sways in directions perpendicular to the support base and is connected to the connection port of the radiation image capturing apparatus.

7. The cassette holder according to claim 1, wherein the connector is urged toward a retention section of the cassette holder, the retention section being configured to hold the radiation image capturing apparatus.

8. The cassette holder according to claim 1 capable of being loaded with radiation image capturing apparatuses having different sizes, the radiation image capturing apparatus having the housing with a rectangular planar profile with two pairs of sides having different lengths and perpendicular to each other.

9. The cassette holder according to claim 8, wherein
while the radiation image capturing apparatus that has a profile with two pairs of sides having different lengths and perpendicular to each other is loaded on the cassette holder, the cassette holder holds the radiation image capturing apparatus so as to allow the radiation image capturing apparatus to rotate on a plane on which the radiation image capturing apparatus lies, and
while the radiation image capturing apparatus that has a profile with four sides having an equal length is loaded on the cassette holder, the cassette holder holds the radiation image capturing apparatus so as to prevent the radiation image capturing apparatus from rotating.

10. The cassette holder according to claim 1, further comprising:
an insertion slot through which the radiation image capturing apparatus is to be inserted; and
a side wall with which the radiation image capturing apparatus is to come into contact and along which the radiation image capturing apparatus is to move, wherein
the side wall is a tilting wall widening toward the insertion slot.

11. The cassette holder according to claim 1 further comprising wheels and a grip.

12. A capturing platform comprising the cassette holder according to claim 1.

13. A mobile radiation image capturing apparatus comprising:
the cassette holder according to claim 1;
a radiation illuminator to emit radiation rays; and
wheels.

* * * * *